US011250932B2

(12) United States Patent
Watts et al.

(10) Patent No.: US 11,250,932 B2
(45) Date of Patent: Feb. 15, 2022

(54) BACTERIAL IDENTIFICATION IN CLINICAL INFECTIONS

(71) Applicant: The Arizona Board of Regents on behalf of the University of Arizona, Tucson, AZ (US)

(72) Inventors: George S. Watts, Tucson, AZ (US); Bonnie L. Hurwitz, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 766 days.

(21) Appl. No.: 15/119,745

(22) PCT Filed: Feb. 18, 2015

(86) PCT No.: PCT/US2015/016319
§ 371 (c)(1),
(2) Date: Aug. 18, 2016

(87) PCT Pub. No.: WO2015/126904
PCT Pub. Date: Aug. 27, 2015

(65) Prior Publication Data
US 2017/0058430 A1  Mar. 2, 2017

Related U.S. Application Data

(60) Provisional application No. 61/941,043, filed on Feb. 18, 2014.

(51) Int. Cl.
*G16B 30/00* (2019.01)
*G16B 35/00* (2019.01)
(Continued)

(52) U.S. Cl.
CPC ............... *G16B 30/00* (2019.02); *C12Q 1/04* (2013.01); *C12Q 1/689* (2013.01); *C12Q 1/6869* (2013.01);
(Continued)

(58) Field of Classification Search
None
See application file for complete search history.

(56) References Cited

U.S. PATENT DOCUMENTS

| 6,283,761 | B1 | 9/2001 | Joao | |
|---|---|---|---|---|
| 2002/0120408 | A1* | 8/2002 | Kreiswirth | G16B 10/00 702/20 |
| 2012/0004111 | A1* | 1/2012 | Colwell | G16B 30/00 506/2 |

OTHER PUBLICATIONS

Faust, K. & Raes, J. Microbial interactions: From networks to models. Nature Reviews Microbiology 10, 538-550 (2012).*

(Continued)

*Primary Examiner* — Soren Harward
(74) *Attorney, Agent, or Firm* — Pabst Patent Group LLP

(57) ABSTRACT

Disclosed herein are methods of identifying infections, such as methods of identifying bacterial infections which utilize whole metagenome sequence analysis to sequence the entire wound microbiome of clinical samples. The disclosed methods use fast k-mer based sequence analysis, predictive modeling, and Bayesian network analysis, to analyze bacterial metagenomic sequence compositions in conjunction with clinical factors to stratify communities of bacteria into healing versus non-healing clusters. The methods of identifying infections can include performing molecular analysis of a patient wound sample, preparing the data obtained from the molecular analysis, diagnosing the wound sample and/or prognosing the wound sample. The disclosed methods can also be used to identify protein function as well as novel biomarkers.

20 Claims, 11 Drawing Sheets

(51) Int. Cl.
| | |
|---|---|
| G16C 20/60 | (2019.01) |
| C12Q 1/04 | (2006.01) |
| C12Q 1/6869 | (2018.01) |
| C12Q 1/689 | (2018.01) |
| G16B 40/30 | (2019.01) |
| G16B 20/20 | (2019.01) |
| G16B 20/00 | (2019.01) |
| G16B 40/00 | (2019.01) |

(52) U.S. Cl.
CPC ............. *G16B 20/00* (2019.02); *G16B 20/20* (2019.02); *G16B 35/00* (2019.02); *G16B 40/30* (2019.02); *G16C 20/60* (2019.02); *C12Q 2600/118* (2013.01); *C12Q 2600/158* (2013.01); *C12Q 2600/16* (2013.01); *G16B 40/00* (2019.02)

(56) References Cited

OTHER PUBLICATIONS

Kunin, V., Copeland, A., Lapidus, A., Mavromatis, K. & Hugenholtz, P. A Bioinformatician's Guide to Metagenomics. Microbiology and Molecular Biology Reviews 72, 557-578 (2008).*
Rosen, G., Sokhansanj, B., Polikar, R., Garbarine, E. & Caseiro, D. Metagenome Fragment Classification Using N-Mer Frequency Profiles. Advances in Bioinformatics 1-12 (2008). doi: 10.1155/2008/205969.*
Thomas, T., Gilbert, J. & Meyer, F. Metagenomics—a guide from sampling to data analysis. Microbial Informatics and Experimentation 2, 3 (2012).*
Bazinet, A. L.; Cummings, M. P. A Comparative Evaluation of Sequence Classification Programs. BMC Bioinformatics 2012, 13 (1), 92.*
Friedman, J.; Alm, E. J. Inferring Correlation Networks from Genomic Survey Data. PLoS computational biology 2012, 8 (9), e1002687.*
Nakamura, S.; Nakaya, T.; Iida, T. Metagenomic Analysis of Bacterial Infections by Means of High-Throughput DNA Sequencing. Experimental Biology and Medicine 2011, 236 (8), 968-971.*
Schmieder, R.; Edwards, R. Fast Identification and Removal of Sequence Contamination from Genomic and Metagenomic Datasets. PLoS ONE 2011, 6 (3), e17288.*
Degnan, et al., "Illumina-based analysis of microbial community diversity", ISME J, 6(1):183-94 (2012).
Dinsdale, et al., "Multivariate analysis of functional metagenomes", Genet, 4:41 (2013).
Hurwitz, et al., "Modeling ecological drivers in marine viral communities using comparative metagenomics and network analyses", PNAS, 111(29):10714-9 (2014).
Huttenhower, "MaSaLin: Multivariate analysis by linear models", https://huttenhower.sph.harvard.edu/maaslin, retrieved Oct. 31, 2016.
Kurtz, et al., "A new method to compute K-mer frequencies and its application to annotate large repetitive plant genomes", BMC Genomics, 9:517 (2008).
Schiemer, "Illumina TruSeq DNA Adapters De-Mystified",Tuffs University,pp. 1-5 2011, https://www.med.unc.edu/pharm/calabreselab/files/tufts-sequenctng-primerm , Retrieved Apr. 17, 2015.
Thomas, et al., "Metagenomics—a guide from sampling to data analysis", Microbial Inform. Exp., 2(1)3 doi 10.1186/2042-5783-2-3 (2012).
International Search Report for PCT/US2015/016319 dated Apr. 30, 2015.
Allers, et al., "Diversity and population structure of Marine Group A bacteria in the Northeast subarctic Pacific Ocean", ISME J., 7(2):256-268 (2013).
Angly, et al., "The marine viromes of four oceanic regions", PLoS Biol., 4(11): e368 (2006).
Bench, et al., "Metagenomic characterization of Chesapeake Bay Virioplankton", Appl. Environ. Microbiol., 73(23):7629-7641 (2007).
Breitbart, et al., "Genomic analysis of uncultured marine viral communities", Proc. Natl. Acad. Sci. USA, 99(22):14250-14255 (2002).
Chiu, et al., "A statistical social network model for consumption data in trophic food webs", Stat. Methodol., 17(4432):139-160 (2014).
Chiu, et al., "A unifying approach for food webs, phylogeny, social networks, and statistics", Proc. Natl. Acad. Sci. USA, 108(38):15881-15886 (2011).
Dinsdale, et al., "Functional metagenomic profiling of nine biomes", Nature, 452(7187):629-632 (2008).
Duhaime, et al., "Ocean viruses: Rigorously evaluating the metagenomic sample-to-sequence pipeline", Virology, 434(2):181-186 (2012a).
Duhaime, et al., "Towards quantitative metagenomics of wild viruses and other ultra-low concentration DNA samples: A rigorous assessment and optimization of the linker amplification method", Environ. Microbiol., 14(9):2526-2537 (2012b).
Edgar, "Search and clustering orders of magnitude faster than BLAST", Bioinformatics, 26(19):2460-2461 (2010).
Edwards, et al., "Viral metagenomics.", Nat. Rev. Microbiol., 3(6):504-510 (2005).
Edwards, et al., "Real time metagenomics: Using k-mers to annotate metagenomes", Bioinformatics, 28(24):3316-3317 (2012).
Henn, et al., "Analysis of high-throughput sequencing and annotation strategies for phage genomes", PLoS ONE, 5(2):e9083 (2010).
Hoff, et al., "Bilinear mixed-effects models for dyadic data", J. Am. Stat. Assoc., 100(469):286-295 (2005).
Hoff, et al., "Latent space approaches to social network analysis", J. Am. Stat. Assoc., 97(460):1090-1098 (2002).
Hoff, et al., "Model averaging and dimension selection for the singular value decomposition", J. Am. Stat. Assoc., 102(478):674-685 (2007).
Hoff, et al., gbme.R. http://www.stat.washington.edu/hoff/Code/hoff_2005_jasa. Accessed on Dec. 31, 2013.
Hoff, et al., gbme.R. http://www2.stat.duke.edu/~pdh10/Code/hoff_2005_jasa/gbme.r., Accessed on Oct. 28, 2020.
Huang, et al., "CD-HIT Suite: A web server for clustering and comparing biological sequences", Bioinformatics, 26(5):680-682 (2010).
Hurwitz, et al., "Evaluation of methods to concentrate and purify ocean virus communities through comparative, replicated metagenomics", Environ. Microbiol. 15(5):1428-1440 (2013a).
Hurwitz, et al., "Metabolic reprogramming by viruses in the sunlit and dark ocean", Genome Biol., 14(11):R123 (2013b).
Hurwitz, et al., The Pacific Ocean virome (POV): A marine viral metagenomic dataset and associated protein clusters for quantitative viral ecology. PLoS ONE 8(2):e57355 (2013c).
Ignacio-Espinoza, et al., "The global virome: Not as big as we thought", Curr. Opin. Virol., 3(5):566-571 (2013).
Jiang, et al., "Comparison of metagenomic samples using sequence signatures", BMC Genomics, 13(730):1-17 (2012).
Kass, et al., "Bayes factors", J. Am. Stat. Assoc., 90(430):773-795 (1995).
Muller, et al., "Model selection in linear mixed models", Stat. Sci., 28(2):135-167 (2013).
Niu, et al., "Artificial and natural duplicates in pyrosequencing reads of metagenomic data", BMC Bioinformatics, 11(187):1-11 (2010).
R Core Team (2012) R: A Language and Environment for Statistical Computing (R Foundation for Statistical Computing, Vienna) (2012). See, e.g., https://www.R-project.org/and https://www.gbif.org/tool/81287/r-a-language-and-environment-for-statistical-computing, accessed Oct. 28, 2020.
Sharon, et al., "Comparative metagenomics of microbial traits within oceanic viral communities", ISME J 5(7):1178-1190 (2011).
Song, et al., "Alignment-free sequence comparison based on next-generation sequencing reads", J. Comput. Biol., 20(2):64-79 (2013).
Supplemental Information: Hurwitz, et al., "Modeling ecological drivers in marine viral communities using comparative metagenomics and network analyses", PNAS, 111(29):10714-9 (2014).
Wilkinson, et al., "Exact and approximate area-proportional circular Venn and Euler diagrams", IEEE Trans. Vis. Comput. Graph., 18(2):321-331 (2012).

(56) References Cited

OTHER PUBLICATIONS

Williamson, et al., "The Sorcerer II Global Ocean Sampling Expedition: Metagenomic characterization of viruses within aquatic microbial samples", PLoS ONE 3(1): e1456 (2008).
Yooseph, et al., "The Sorcerer II Global Ocean Sampling expedition: Expanding the universe of protein families", PLoS Biol., 5(3):e16 (2007).
Zhang, et al., "These are not the k-mers you are looking for: Efficient online k-mer counting using a probabilistic data structure", PLOS Biology, (2013).

* cited by examiner

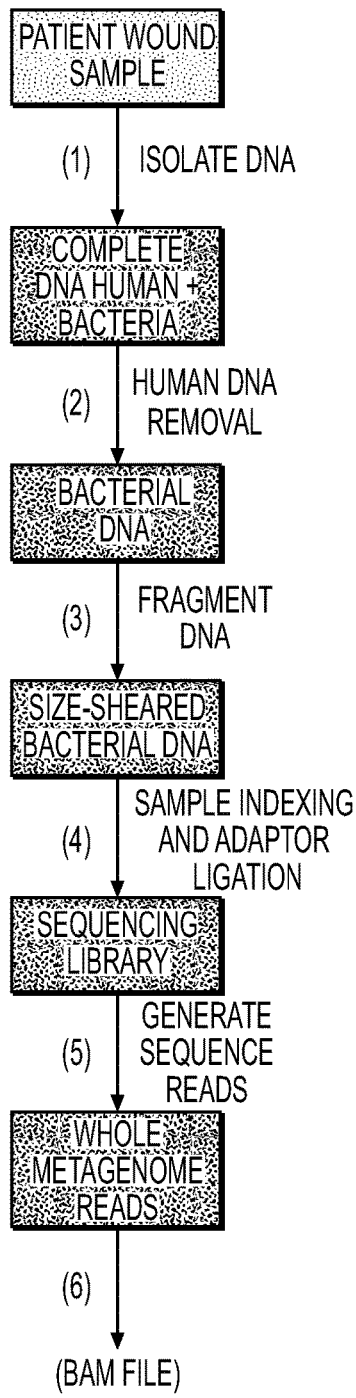

MOLECULAR ANALYSIS PIPELINE DETAIL (1) TOTAL DNA FROM THE PATIENT SAMPLE IS ISOLATED AS THE FIRST STEP TOWARDS SEQUENCING.

(2) DIAGNOSIS AND PROGNOSIS IS DEPENDENT ON ANALYSIS OF BACTERIAL DNA, THEREFORE HUMAN DNA SHOULD BE REMOVED AS MUCH AS POSSIBLE FROM THE SAMPLE.

(3) IN PREPARATION FOR DNA SEQUENCING THE BACTERIAL DNA MUST BE FRAGMENTED TO APPROPRIATE LENGTH FOR THE SEQUENCING PLATFORM THAT WILL BE UTILIZED.

(4) PLATFORM-SPECIFIC SEQUENCING ADAPTORS MUST BE LIGATED TO THE BACTERIAL DNA FRAGMENTS FOR SEQUENCING. IN ADDITION, MULTIPLE PATIENT SAMPLES MAY BE MOLECULARLY BARCODED AT THIS STEP TO TAKE ADVANTAGE OF THE HIGH-THROUGHPUT CAPACITY OF MOST SEQUENCING PLATFORMS.

(5) REGARDLESS OF SEQUENCING PLATFORM CHOSEN, THE SEQUENCE OF NUCLEIC ACIDS WITHIN EACH DNA FRAGMENT IS ANALYZED AND CONVERTED TO AN ELECTRONIC SIGNAL CALLED A "READ"

(6) THE READS FROM EACH SAMPLE ARE SUMMARIZED IN A STANDARD BINARY FORMAT REFERRED TO AS A "BAM FILE". BAM FILES ARE SEQUENCING PLATFORM INDEPENDENT AND READY FOR BIOINFORMATIC ANALYSIS.

*FIG. 2*

DATA PREPARATION PIPELINE DETAIL (7) STARTING WITH THE BAM FILE OF READS, SEVERAL QUALITY CONTROL STEPS ARE UNDERTAKEN TO PREPARE THE READS FOR ANALYSIS. THESE STEPS INCLUDE: QUALITY TRIMMING, LENGTH FILTERING, SEQUENCING ADAPTER REMOVAL, AND BINNING OF READS BY MOLECULAR BARCODE.

(8) MOLECULAR REMOVAL OF HUMAN DNA WILL NOT BE ABSOLUTE. THEREFORE, QUALITY CONTROLLED READS WILL BE ALIGNED TO A CURRENT REFERENCE HUMAN GENOME (E.G. HG19). READS ALIGNING TO THE REFERENCE HUMAN GENOME WILL BE REMOVED FROM THE ANALYSIS.

(9) READS WILL BE BROKEN INTO k-mers OF APPROXIMATELY ~20 BASE PAIRS. THESE k-mers ARE THEN INDEXED IN A SUFFIX ARRAY FOR RAPID ANALYSIS.

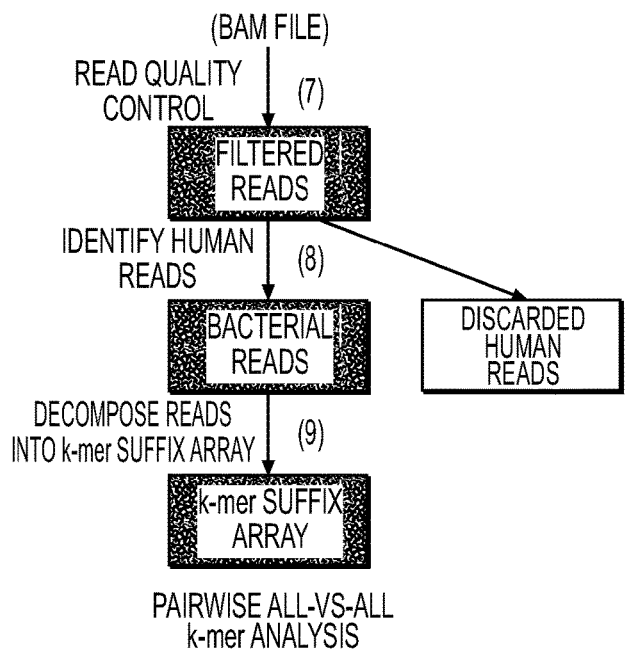

*FIG. 3*

CLINICAL PROGNOSIS PIPELINE DETAIL

(12) FOR THE PURPOSE OF PROGNOSIS, k-mers FROM PATIENT DERIVED READS ARE COMPARED TO PRIOR CLINICAL SAMPLES FOR WHICH OUTCOME IS KNOWN.

(13) AS WITH DIAGNOSIS, READ ABUNDANCE IS ESTIMATED FROM THE ABOVE k-mer ANALYSIS AND USED TO GENERATE A READ ABUDANCE MATRIX RELATIVE TO PRIOR PATIENT SAMPLES OF KNOWN OUTCOME.

(14) THE READ ABUNDANCE MATRIX IS SUBSAMPLED MANY TIMES USING A BAYSIAN SOCIAL NETWORK ANALYSIS UNTIL CONVERGENCE IS REACHED. SIMULTANEOUSLY, LINEAR REGRESSION IS PERFORMED ON METADATA DERIVED FROM THE DIAGNOSIS IN STEP 10 AS WELL AS POTENTIALLY SIGNIFICANT PATIENT DATA (E.G. RISK FACTORS).

(15) THE POSITION OF A PATIENT SAMPLE WITHIN THE SOCIAL NETWORK MAP DERIVED FROM THE BAYSIAN ANALYSIS CAN BE ANALYZED STATISTICALLY TO PREDICT THE PATIENT'S CLINICAL OUTCOME THEREBY HELPING TO GUIDE PHYSICIAN DECISION MAKING.

(16) READS DIVING THE SEPARATION BETWEEN SAMPLES IN THE SOCIAL NETWORK MAP CAN BE EXTRACTED AND USED IN BIOMARKER DEVELOPMENT AND PROVIDE A STARTING POINT FOR IDENTIFYING THE BIOLOGICAL PATHWAYS DRIVING PATIENT OUTCOMES.

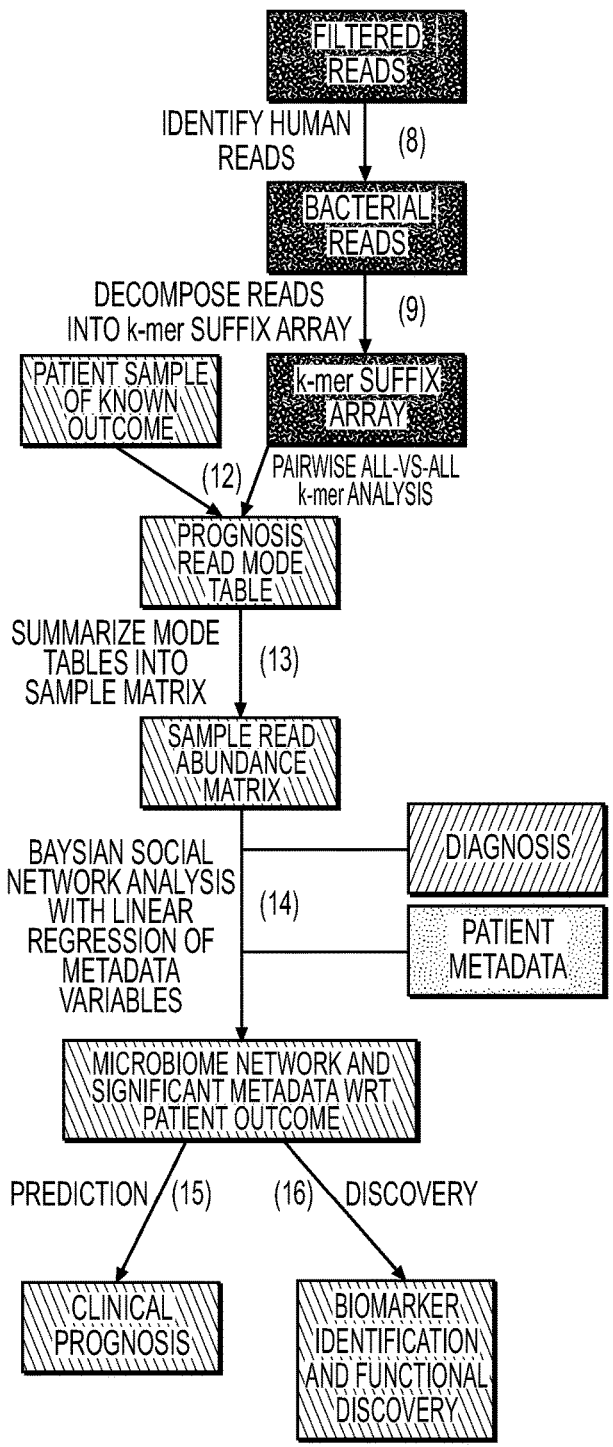

FIG. 5

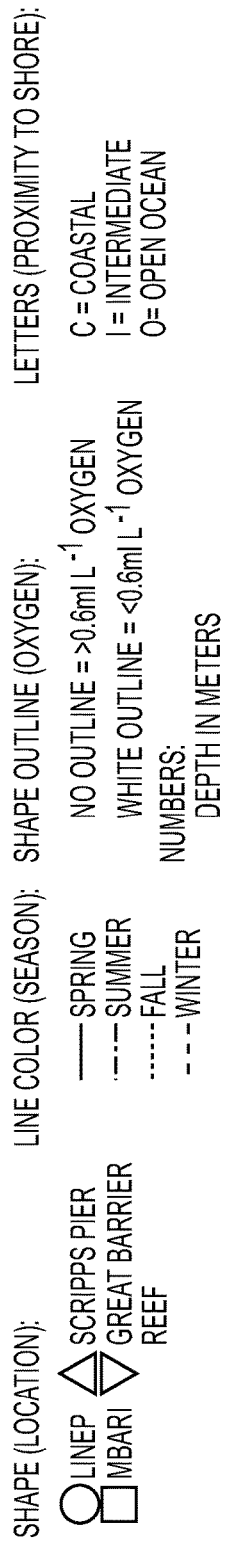
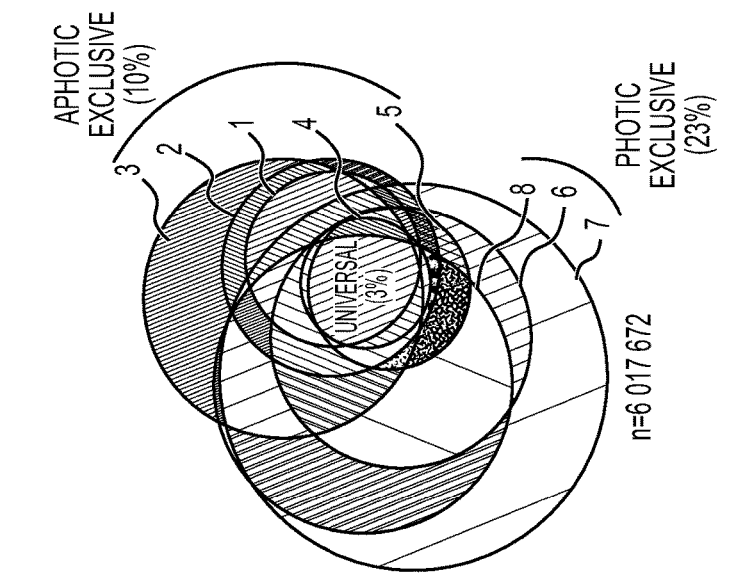
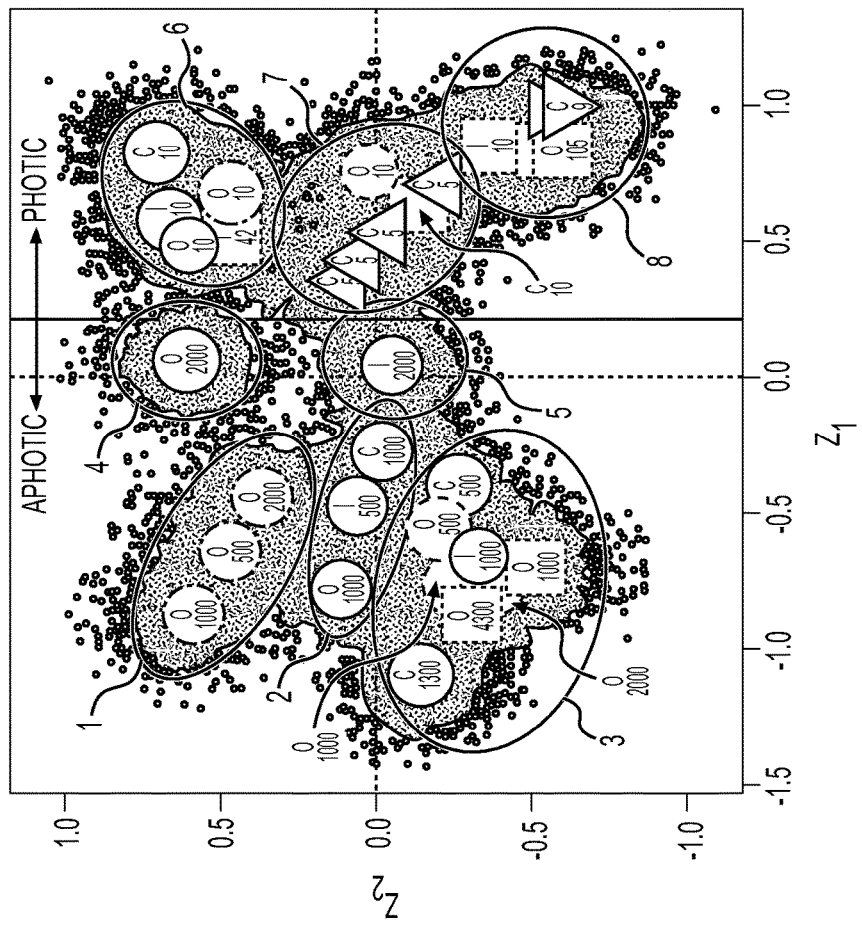
FIG. 7A
FIG. 7B

BACTERIAL IDENTIFICATION IN CLINICAL INFECTIONS

CROSS REFERENCE TO RELATED APPLICATIONS

This application is a 371 application of International Application No. PCT/US2015/016319, filed Feb. 18, 2015, which claims priority to and the benefit of U.S. Provisional Application No. 61/941,043, filed Feb. 18, 2014, which is hereby incorporated by reference in its entirety.

FIELD

This disclosure relates to bacterial identification and in particular, to use of whole genome sequence analysis for bacterial identification in the diagnosis and prognosis of clinical infections.

BACKGROUND

Clinical infections are a significant cause of mortality and morbidity in human health. Appropriate treatment of bacterial infections requires accurate diagnosis of the species present and any antibiotic resistance or virulence factors they may possess. Current methods of bacterial identification include culture-based techniques, mass spectrometry, and sequencing of conserved bacterial genes. Culture-based methods are limited by length of time to diagnosis (24-72 hours), bias in species detected, and lack of sensitivity (e.g., fastidious organisms). Mass spectrometry though inexpensive and rapid, requires a pure culture sample therefore imposing similar limitations as culture-based methods. Typically only 20-40% of samples can be diagnosed using standard culture-based methods. Next generation sequencing (NGS) techniques offer a viable alternative, wherein the organisms in a clinical sample can be sequenced in an unbiased and culture-independent manner. One technique is to sequence highly conserved genes (e.g., 16s rRNA, rpoB, atpD, infB) to differentiate species based on small-scale variation in sequence composition. This technique is limited however because it lacks specificity for organisms with highly similar sequences in the targeted genes.

The deficiencies and biases of currently used methods often leave clinicians with no choice but to use empirically based antibiotic regimens that can be ineffective and contribute to the rise of antibiotic resistance, with serious world-wide health implications. In the case of diabetic foot ulcers and other polymicrobial infections, the current lack of knowledge of the diversity, composition and proportions of microbial communities inhibits the ability to understand why infections become chronic or heal. Moreover, by looking at an infection, clinicians cannot predict which patients will be responsive to basic treatments and heal, or will become non-healers requiring advanced treatments such as pressure bandages. Patients are treated with advanced therapies, as standard therapies fail, losing valuable time to prevent the spread of infection that often leads to further complications including amputation of the affected limb.

SUMMARY

Disclosed herein are methods of diagnosing and prognosing infections, such as methods of identifying bacterial, viral, parasitic and/or fungal species utilizing whole metagenome sequence analysis to define the entire microbiome in clinical samples, such as from diabetic foot ulcers. In some embodiments, the disclosed methods use next-generation sequencing, preparation of the data, fast k-mer based sequence analysis, and Bayesian network analysis to analyze the composition of samples. In conjunction with clinical factors, the methods can be used to stratify communities of the desired organism, such as bacteria, viral, parasitic and/or fungal species into healing versus non-healing clusters for prognosing infections, such as infections in wounds, as well as diagnosing species present along with their capability to produce drug resistance and virulence proteins (see FIG. 1). In contrast, to sequencing specific genes for identification of the organism (e.g., bacteria, virus, fungus or parasite), the method disclosed herein uses the entire metagenomic to assess the composition of mono- or polymicrobial infections. This method is of particular utility for diagnosis of closely related species that are indistinguishable by 16s rRNA sequence along that have functional differences that make them clinically distinct (e.g., distinguishing between normal enteric *Escherichia coli* and enterohemorrhagic strains).

Because sequence reads that represent significant patterns in the network can be mined out of the analysis, this approach drives functional comparative metagenomic analyses. This is also relevant pragmatically in terms of runtime because fewer reads require extensive functional annotation. Moreover, the remaining unknown fraction of reads exclusive to a certain part of the network provides a starting point for future empirical analyses to understand the functional differences between bacteria that drive patient outcome. This approach is broadly applicable to metagenomes comprised of any microbe from viruses to parasites to bacteria or fungi and extends current approaches through the use of whole metagenomes and a comprehensive statistical framework. Thus, the disclosed methods can be used to identify functional protein motifs as well as novel biomarkers that can be used to mechanistically understand differences in patient outcome and as the basis for development of rapid diagnostic/prognostic tests.

The Bayesian network approach to analyze bacterial composition and abundance disclosed herein provides a significant advance over alternative methods for dimensionality reduction such as principle components analysis (PCoA) and nonmetric multi-dimensional scaling (nMDS). Broadly, the contrast lies in the fact that PCoA and nMDS are generally descriptive approaches (Dinsdale et al. (2013) *Front Genet* 4: 41) whereas the network approach detailed here provides a full inferential framework. Specifically, relational data methods are used to create a dependence structure in ordination space that includes random effects, and as a result allows for the proper inference for regression coefficients (i.e. metadata). In simple terms, the distances between bacterial species based on shared sequence motifs can be visually represented, while at the same time accounting for biological factors in a single statistical model (see, for example, Hurwitz, et al., *PNAS* 111.29 (2014): 10714-10719).

This approach is also inherently different from other statistical frameworks (e.g., MaAsLin (Huttenhower (2014). MaAsLin: Multivariate Analysis by Linear Models. See domain name huttenhower.sph.harvard.edu/maaslin) that identify associations between metadata and the abundance of operational taxonomic units (OTUs) or functions in metagenomic samples. Specifically, MaAsLin outputs a list of OTUs or functions that are significant given a metadata type. Given that the results are granular (by OTU or function) and only account for only one metadata type at a time, they cannot be combined. In contrast, the disclosed analytical framework uses a model that enables simultaneous examination of shared sequence space between bacterial genomes in conjunction with multiple metadata types, and requires no prior organizational "bins" (e.g., OTUs for MaAsLin). Both advances are key for surveying complex bacterial communities to look for drivers of treatment decisions and patient outcomes.

Also disclosed herein is a system capable of performing the disclosed methods. The system comprises one or more processors and memory coupled to the one or more processors which encodes one or more programs. The programs encoded in memory cause the one or more processors to perform the steps of the disclosed methods. Also disclosed are one or more non-transitory computer-readable media for identifying infection in a sample, the non-transitory computer-readable media storing instructions that when executed cause a computer to perform the methods disclosed herein.

The foregoing and other features and advantages of the disclosure will become more apparent from the following detailed description, which proceeds with reference to the accompanying figures.

BRIEF DESCRIPTION OF THE DRAWINGS

FIG. 2 is a detailed schematic of the molecular analysis performed in an exemplary method for identifying bacterial infections.

FIG. 3 is detailed schematic of data preparation performed in an exemplary method for identifying bacterial infections.

FIG. 5 is detailed schematic of clinical prognosis performed in an exemplary method for identifying bacterial infections.

FIGS. 7A-7D are diagrams showing the relationships between marine viral communities.

FIG. 10 illustrates that the pure strains form different clusters based on their sequence that will allow one to place unknown clinical isolates in a "clinical bacterial sequence map". For example, one can also see differences in closely related strains (e.g., *S. aureus* with methicillin sensitive (MSSA) versus with methicillin resistant *Staphylococcus aureus* (MRSA)).

DETAILED DESCRIPTION OF SEVERAL EMBODIMENTS

I. Introduction

Figure 1:
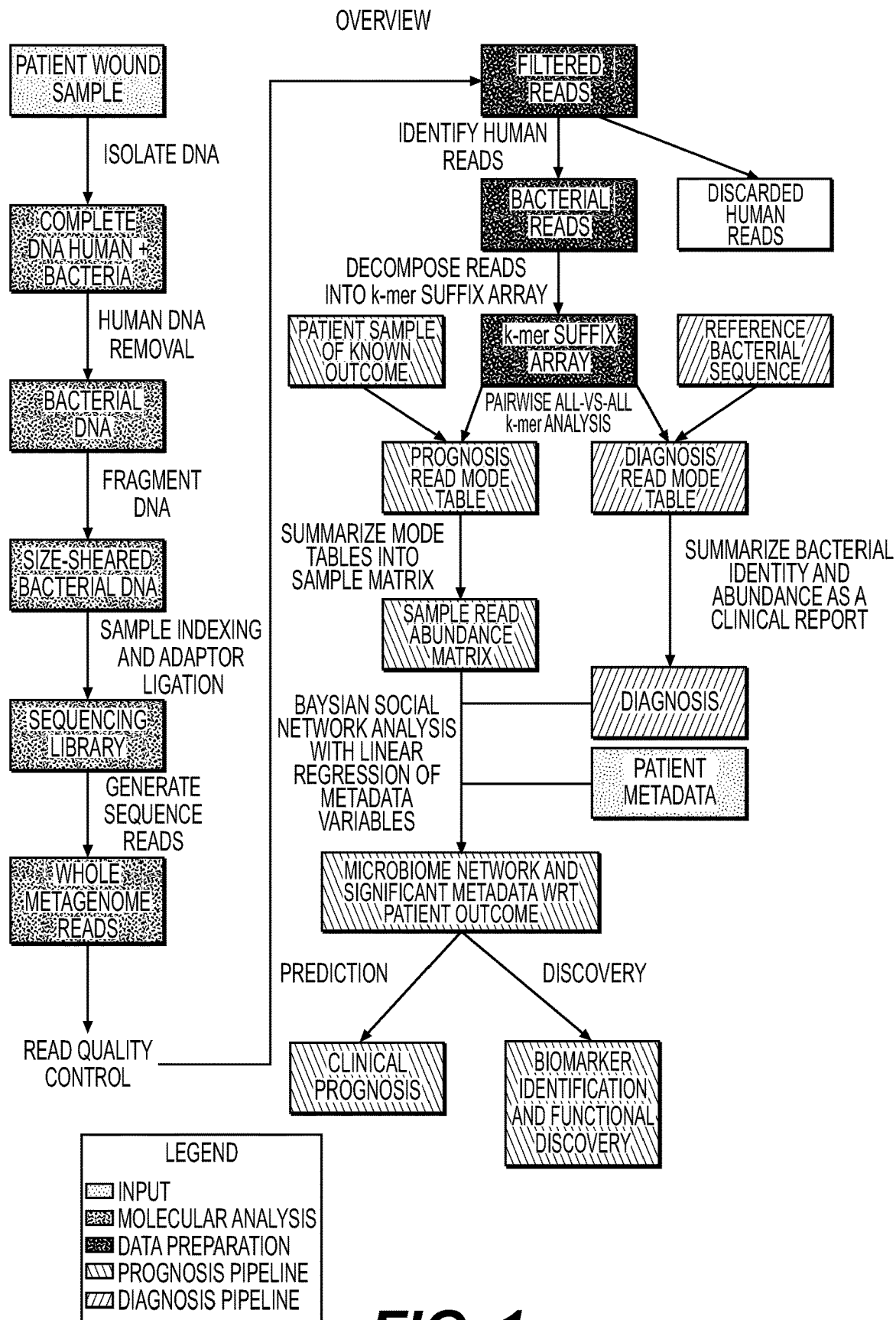
FIG. 1 is schematic of an overview of an exemplary method for identifying bacterial infections which includes sample preparation, DNA extraction and purification, sequencing, bioinformatics analyses, k-mer comparisons, network and regression analysis.

Methods of diagnosing and prognosing infections, such as bacterial, viral, parasitic and/or fungal which utilize whole metagenome sequencing of the selected microbiome, such as a wound microbiome, from clinical samples are provided. The disclosed methods use fast k-mer based sequence analysis, and Bayesian network analysis, to analyze bacterial metagenomic sequence in conjunction with clinical factors to diagnose wound compositions at the species level and stratify communities of bacteria into healing versus non-healing clusters (see FIG. 1). Moreover, components of networks can be mined for additional unexpected correlations in addition to identifying the presence of antibiotic resistance and virulence factors. For example, directed questions can be asked using electronic health data from patients that fall into healing vs. non-healing components of the network to look for significant clinical drivers and microbial community composition of poor outcomes. These networks and underlying metadata are fundamental in generating testable hypotheses about wound care and management. Further, given a "healing map" (e.g., a network of patient samples with known prior wound outcomes) clinicians can map new samples by metagenomic sequence composition to predict the best course of treatment. This map can be used to differentiate chronic wounds before they become chronic so that advanced therapies can be applied at diagnosis rather than after lack of response to empirically based treatments. By analyzing the genomic sequences of all species in an infection the disclosed methods identify and quantify sequences that function as biomarkers for predicting clinical outcomes through correlation with prior clinical "phenotypes." This not only allows one to identify what species are present and their abundance, but also the ability to predict the behavior of the infection and how it will respond to available therapies and clinical options for directed patient care using prior data sets. Thus, the whole genome sequence analysis and big data analytics provide complete knowledge of the wound flora and their inherent resistance and virulence, thereby allowing clinicians to make fact-based decisions about treatment options. These methods can be utilized to improve clinical outcomes in many types of infections, including, but not limited to, diabetic foot ulcers (DFUs), sepsis, and nosocomial infections.

The disclosed methods can change the standard of care for human infection in general. Currently, a diabetic foot ulcer is swabbed to collect a sample of bacteria and sent for culture or gene-based sequencing for diagnosis of the species present. If the culture or gene-based sequencing process is successful, dominant bacteria and antibiotic resistance can potentially be identified. However, the process is time consuming and in a significant number of cases leads to no diagnosis or incomplete information (e.g., 16s rRNA sequencing cannot identify the presence of drug resistance genes). Culturing is even less effective for patients who have prior antibiotic therapy or are infected with fastidious organisms, such as bacteria, fungi, viruses and/or parasites. The disclosed methods are superior to those currently used for several reasons, including the following: (1) metagenomics is culture independent and gives an unbiased representation of the community composition; (2) the computational method disclosed does not require sequence assembly or gene annotation from known organisms that could misrepresent the community due to database bias or assembly issues; (3) the method provides a visualization of patient samples in a network that can be used for clinical prognosis based on prior samples with known clinical outcomes; and (4) the approach is scalable given low cost for DNA sequencing, fast k-mer based sequence analysis algorithms, and distributive cloud computing capabilities. The presently disclosed methods provide a unified statistical framework for evaluating genetic predictors of community structure based on multiple variables that can be dependent on one another by employing a Bayesian network analysis (for visualization), such as a Bayesian social network analysis, in conjunction with a regression analysis (to define clinical factors that predict the structure of the network).

The disclosed methods are believed to be useful for not only the prediction of clinical outcomes associated with certain bacterial infections, such as diabetic foot ulcers, but broadly applicable to any mono- or polymicrobial clinical sample. For example, the methods could be applied to time-sensitive applications such as diagnosing sepsis or nosocomial infection. The methods can also be applied to a variety of infections including those that are fungal or viral in origin (Hurwitz B L, Westveld A H, Brum J R, & Sullivan M B (2014) Modeling ecological drivers in marine viral communities using comparative metagenomics and network analyses. *PNAS*, which is hereby incorporated by reference in its entirety and FIGS. 7A-7D).

It is contemplated that the disclosed methods can be used to: (1) generate diagnoses from large-scale next-generation sequence datasets comprising infection derived metagenomes given a constant influx of new patient samples, (2) develop predictive models to associate microbial community sequence composition with clinical outcomes, (3) produce networks to visualize new patient samples in relation to samples with known clinical outcomes to inform care, and (4) develop a big data analytic toolkit for rapid data processing thereby enabling bench to bedside applications of the work. For example, applicable big data toolkits could include large-scale data structures such as Hadoop and noSQL platforms such as Neo4J and MongoDB. Specifically, for prognosis using 1000's of samples, the k-mer data can be pre-computed and stored on commodity servers in a Hadoop Big Data architecture. This allows for comparison of a new metagenome (from a patient sample) against 1000's of existing samples with known diagnosis, without having to re-compute the reference dataset therefore speeding processing time for analysis and commercialization of the technique.

II. Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). As used herein and in the appended claims, the singular forms "a", "an", and "the" include plural referents unless the context clearly dictates otherwise. Unless defined otherwise, all technical and scientific terms used herein have the same meaning as commonly understood to one of ordinary skill in the art to which this disclosure belongs. "Comprising" means "including." All publications, patent applications, patents, and other references mentioned herein are incorporated by reference in their entirety.

Bacteria: A large domain of prokaryotic microorganisms. Typically a few micrometres in length, bacteria have a wide range of shapes, ranging from spheres to rods and spirals. There are broadly speaking two different types of cell wall in bacteria, called Gram-positive and Gram-negative. Gram-positive bacteria possess a thick cell wall containing many layers of peptidoglycan and teichoic acids. In contrast, Gram-negative bacteria have a relatively thin cell wall consisting of a few layers of peptidoglycan surrounded by a second lipid membrane containing lipopolysaccharides and lipoproteins. Most bacteria have the Gram-negative cell wall, and only the Firmicutes and Actinobacteria have the alternative Gram-positive arrangement.

Bayesian network: A probabilistic graphical model that represents a set of random variables and their conditional dependencies via a directed acyclic graph. For example, the Bayesian network embodied herein for diagnosis represents the probabilistic presence of bacterial species given observed k-mers derived from DNA sequence. Similarly, one can envision a Bayesian network for prognosis that represents the probabilistic presence of a bacterial community associated with a chronic non-healing wound.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal (termination codon). The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a protein, or a fragment thereof, encompasses both the sense strand and its reverse complement. Thus, for instance, it is appropriate to generate probes or primers from the reverse complement sequence of the disclosed nucleic acid molecules.

Gene: A segment of DNA that contains the coding sequence for a protein, wherein the segment may include promoters, exons, introns, and other untranslated regions that control expression.

Fungus: Living, single-celled and multicellular organisms belonging to the kingdom Fungi. Most species are characterized by a lack of chlorophyll and presence of chitinous cell walls, and some fungi may be multinucleated.

k-mer: A specific n-tuple or n-gram of nucleic acid or amino acid sequences that can be used to identify certain regions within biomolecules like DNA (e.g., for gene prediction) or proteins. In this embodiment, a k-mer is a short DNA sequence of length "n" typically ranging from 20-100 base pairs derived from metagenomic sequence data.

Parasite: An organism that lives inside humans or other organisms acting as hosts (for the parasite). Parasites are dependent on their hosts for at least part of their life cycle. Parasites are harmful to humans because they consume needed food, eat away body tissues and cells, and eliminate toxic waste, which makes people sick.

Probes and primers: A probe comprises an isolated nucleic acid capable of hybridizing to a target nucleic acid. A detectable label or reporter molecule can be attached to a probe or primer. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example in Sambrook et al. (In Molecular Cloning: A Laboratory Manual, CSHL, New York, 1989) and Ausubel et al. (In Current Protocols in Molecular Biology, John Wiley & Sons, New York, 1998).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, or more contiguous nucleotides complementary to the target nucleic acid molecule, such as 20-70 nucleotides, 20-60 nucleotides, 20-50 nucleotides, 20-40 nucleotides, or 20-30 nucleotides.

Primers are short nucleic acid molecules, for instance DNA oligonucleotides are 10 nucleotides or more in length, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50, 55, 60, 65, 70 or more consecutive nucleotides. In particular examples, a primer is at least 15 nucleotides in length, such as at least 15 contiguous nucleotides complementary to a target nucleic acid molecule. Particular lengths of primers that can be used to practice the methods of the present disclosure include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, at least 55, at least 60, at least 65, at least 70, or more contiguous nucleotides complementary to the target nucleic acid molecule to be amplified, such as a primer of 15-70 nucleotides, 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction.

Nucleic acid probes and primers can be readily prepared based on the nucleic acid molecules provided herein. It is also appropriate to generate probes and primers based on fragments or portions of these disclosed nucleic acid molecules, for instance regions that encompass the identified polymorphisms of interest. PCR primer pairs can be derived from a known sequence by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Sample: A sample, such as a biological sample, is a sample obtained from a subject. As used herein, biological samples include all clinical samples useful for identifying infection, such as bacterial infection, in a subject, including, but not limited to, cells, tissues, and bodily fluids (such as saliva); biopsied or surgically removed tissue, including tissues that are, for example, unfixed, frozen, fixed in formalin and/or embedded in paraffin; tears; skin scrapes; or surface washings. In a particular example, a sample includes cells collected by using a swab or by an oral or topical rinse.

Subject: Living multi-cellular vertebrate organisms, a category that includes human and non-human mammals (such as laboratory or veterinary subjects).

Taxonic composition: Refers to relative abundance of certain taxa in a sample and the relationship with clinical outcome.

Virus: A microscopic infectious organism that reproduces inside living cells. A virus consists essentially of a core of nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

III. Methods of Use

Disclosed herein are methods of identifying infections, such as methods of identifying bacteria, fungal, viral and/or parasitic infections which utilize whole metagenome sequence analysis to sequence the entire microbiome of clinical samples, such as the entire wound microbiome. These methods can be used to diagnose and prognose infections. In some embodiments, the methods include performing molecular analysis of a patient wound sample, preparing the data obtained from the molecular analysis, diagnosing the wound sample and/or prognosing the wound sample. Although the methods described in detail below focus upon bacterial infections, it is contemplated that the disclosed methods can be utilized to improve clinical outcomes in many types of infections, including, but not limited to, viral, fungal, and parasitic infections. In some examples, the disclosed methods are used to diagnose and prognose diabetic foot ulcers (DFUs), sepsis and/or nosocomial infection. In some examples, the disclosed methods are used to identify biomarkers and/or protein function.

i. Type of Organism Detected in Sample

The disclosed method may be used to identify infections, such as bacteria, fungal, viral and/or parasitic infections. In one example, one or more of the following types of organisms can be detected by the present method: *Abiotrophia, Acanthamoeba, Acetobacteraceae, Achromobacter, Acidaminococcus, Acidithiobacillus, Acidocella, Acidovorax, Acinetobacter, Acremonium, Actinobacillus, Actinobaculum, Actinomadura, Actinomyces, Adenovirus, Aerococcus, Aeromonas, Aeropyrum, Aggregatibacter, Agrobacterium, Akkermansia, Alcaligenes, Alistipes, Alphacoronavirus, Alternaria, Alteromonas, Anabaena, Anaero-* biospirillum, Anaerococcus, Anaeroglobus, Anaerostipes, Anaplasma, Anoxybacillus, Aquabacterium, Arachnia, Aranicola, Arcanobacterium, Arcobacter, Arthrobacter, Arthroderma, Arthrospira, Ascaris, Aspergillus, Astrovirus, Atopobium, Bacillus, Bacteroides, Bacteroidetes, Bartonella, Beauveria, Betacoronavirus, Bifidobacterium, Bilophila, Bipolaris, Blastochloris, Blastococcus, Blastocystis, Blastomyces, Blastoschizomyces, Blautia, Bordetella, Borrelia, Brachymonas, Brachyspira, Bradyrhizobium, Branhamella, Brevibacillus, Brevibacterium, Brevundimonas, Brucella, Buchnera, Bulleidia, Burkholderia, Burkholderiales, Buttiauxella, butyrate producing organism, Butyrivibrio, Calicivirus, Campylobacter, Candida, Candidatus, Capnocytophaga, Carbolfuchsin, Cardiobacterium, Carnobacterium, Catenibacterium, Caulobacter, Cedecea, Cefuroxime, Cellulosimicrobium, Centipeda, Cephalosporins, Cephalosporium, Chaetomium, Chaetothyriales, Chilomastix, Chlamydia, Chlamydophila, Chromobacterium, Chryseobacterium, Chrysosporium, Citrobacter, Cladosporium, Clarithromycin, Clindamycin, Cloacibacterium, Clonorchis, Clostridiales, Clostridium, Coccidioides, Collinsella, Comamonas, Conidiobolus, Coprobacillus, Coprococcus, Corynebacteria, Corynebacterium, Coxiella, Cryptobacterium, Cryptococcus, Cryptosporidium, Cunninghamella, Curvularia, Cyanobacteria, Cyclospora, Cylindrospermopsis, Cytomegalovirus, Dactylaria, Davidiella, Delftia, Deltacoronavirus, Dermabacter, Desmospora, Desulfitobacterium, Desulfomicrobium, Desulfovibrio, Dialister, Didymella, Dientamoeba, Diphyllobothrium, Dolosigranulum, Dorea, Dreschlera, Eboli, Echinococcus, Edwardsiella, Eggerthella, Ehrlichia, Eikenella, Empedobacter, Enhydrobacter, Entamoeba, Enterobacter, Enterobacteriaceae, Enterobius, Enterococci, Enterococcus, Enterovirus, Epicoccum, Epidermophyton, Eremococcus, Erwinia, Erysipelothrix, Erysipelotrichaceae, Erythrobacter, extended spectrum beta-lactamase(ESBL), Escherichia, Eubacterium, Ewingella, Excerohilum, Exiguobacterium, Exoantigen, Exophiala, Facklamia, Faecalibacterium, Filifactor, Finegoldia, Flavobacterium, Flavonifractor, Fonsecaea, Francisella, Frankia, Fusarium, Fusobacterium, Gallicola, Gammacoronavirus, Gardnerella, Gemella, Geobacillus, Geotrichum, Giardia, Giemsa, Gliocladium, Gordonia, Gordonibacter, Granulicatella, Haemophilus, Hafnia, Haloarcula, Halobacterium, Halosimplex, Hansenula, Helcococcus, Helicobacter, Helminthosporium, Hemadsorbing, Herpes, Histoplasma, Holdemania, Hymenolepis, Hyphomicrobium, Iodamoeba, Isospora, Janibacter, Janthinobacterium, Jeotgalicoccus, Johnsonella, Kingella, Klebsiella, Kluyvera, Kocuria, Koserella, Lachnospiraceae, Lactobacillus, Lactococcus, Lautropia, Leclercia, Legionella, Leifsonia, Leminorella, Leptospira, Leptotrichia, Leuconostoc, Listeria, Listonella, Lyngbya, Lysinibacillus, Malassezia, Malbranchea, Mannheimia, Megamonas, Megasphaera, Mesorhizobium, Methanobacterium, Methanobrevibacter, Methanosaeta, Methanosarcina, Methanothermobacter, Methylobacterium, Microbacterium, Micrococcus, Microcoleus, Microcystis, Microsporidia, Microsporum, Mobiluncus, Mogibacterium, Mollicutes, Moraxella, Morganella, Mycelia, Mycetocola, Mycobacterium, Mycoplasma, Myroides, Neisseria, Neorickettsia, Nigrospora, Nocardia, Nodularia, Nostoc, Oceanobacillus, Ochrobactrum, Odoribacter, Oenococcus, Oerskovia, Oligella, Olsenella, Oribacterium, Ornithobacterium, Oscillatoria, Oxalobacter, Paecilomyces, Paenibacillus, Pantoea, Parabacteroides, Paracoccus, Paraprevotella, Parascardovia, Parasutterella, Parvimonas, Pasteurella, Pediculus, Pediococcus, Penicillium, Peniophora, Peptococci, Peptococcus, Peptoniphilus, Peptostreptococcus, Petrobacter, Phaeoacremonium, Phaeoannellomyces, Phascolarctobacterium, Phialemonium, Phialophora, Photobacterium, Photorhabdus, Phyllobacterium, Pichia, Picornavirus, Pirellula, Piscirickettsia, Plankthothrix, Planomicrobium, Plasmodium, Plesiomonas, Pneumocystis, Poliovirus, Porphyromonas, Prevotella, Propionibacterium, Proteus, Prototheca, Providencia, Pseudallescheria, Pseudomonas, Pseudoramibacter, Pseudoxanthomonas, Rahnella, Ralstonia, Raoultella, Rathayibacter, Rhinocladiella, Rhinosporidium, Rhinovirus, Rhizobium, Rhizomucor, Rhizopus, Rhodococcus, Rhodopirellula, Rhodopseudomonas, Rhodotorula, Riemerella, Roseburia, Roseomonas, Rotavirus, Rothia, Ruminococcaceae, Ruminococcus, Saccharomyces, Salmonella, Sarcoptes, Scardovia, Scedosporium, Schistosoma, Schizophyllum, Schlegelella, Scopulariopsis, Scytalidium, Segniliparus, Selenomonas, Sepedonium, Serratia, Shewanella, Shigella, Simonsiella, Sistotrema, Slackia, Sneathia, Solobacterium, Sphingobacterium, Sphingobium, Sphingomonas, Spirochaeta, Spirochaetaceae, Spirochetes, Spirosoma, Sporobolomyces, Sporothrix, Stachybotrys, Staphylococcus, Stemphylium, Stenotrophomonas, Stenoxybacter, Streptococcus, Streptomyces, Strongyloides, Succinatimonas, Succinivibrio, Sutterella, Syncephalastrum, Synechococcus, Synergistetes, Taenia, Tannerella, Tatumella, Tepidimonas, Tetragenococcus, Tissierella, Treponema, Trichinella, Trichoderma, Trichomonads, Trichomonas, Trichophyton Trichosporon, Trichothecium, Trichuris, Tropheryma, Trypanosoma, Turicibacter, Udeniomyces, Ulocladium, Ureaplasma, Ureibacillus, Ustilago, Vagococcus, Varicella, Variovorax, Veillonella, Verticillium, Vibrio, Virgibacillus, Viridans, Vulcanisaeta, Wangiella, Wautersia, Weeksella, Weissella, Wolbachia, Wolinella, Xanthomonas, Xylohypha, Yersinia, Yokenella, Zoogloea, or Zygomycete.

In some examples, one or more pathogenic bacteria are detected with the disclosed method. Examples of pathogenic bacteria which could be detected with the disclosed methods include without limitation any one or more of (or any combination of) *Acinetobacter baumanii*, *Actinobacillus* sp., Actinomycetes, *Actinomyces* sp. (such as *Actinomyces israelii* and *Actinomyces naeslundii*), *Aeromonas* sp. (such as *Aeromonas hydrophila*, *Aeromonas veronii* biovar *sobria* (*Aeromonas sobria*), and *Aeromonas caviae*), *Anaplasma phagocytophilum*, *Anaplasma marginal,e Alcaligenes xylosoxidans*, *Acinetobacter baumanii*, *Actinobacillus actinomycetemcomitans*, *Bacillus* sp. (such as *Bacillus anthracis*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis* and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melintensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetii*, *Corynebacterium* sp. (such as, *Corynebacterium diphtheriae*, *Corynebacterium jeikeum* and *Corynebacterium*), *Clostridium* sp. (such as *Clostridium perfringens*, *Clostridium difficile*, *Clostridium botulinum* and *Clostridium tetani*), *Eikenella corrodens*, *Enterobacter* sp. (such as *Enterobacter aerogenes*, *Enterobacter agglomer-* ans, *Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*, *Helicobacter* sp. (such as *Helicobacter pylori*, *Helicobacter cinaedi* and *Helicobacter fennelliae*), *Kingella kingii*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Mannheimia hemolytica*, *Moraxella catarrhalis*, *Morganella* sp., *Mobiluncus* sp., *Micrococcus* sp., *Mycobacterium* sp. (such as *Mycobacterium leprae*, *Mycobacterium tuberculosis*, *Mycobacterium paratuberculosis*, *Mycobacterium intracellulare*, *Mycobacterium avium*, *Mycobacterium bovis*, and *Mycobacterium marinum*), *Mycoplasm* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (such as *Neisseria gonorrhoeae* and *Neisseria meningitidis*), *Pasteurella multocida*, *Plesiomonas shigelloides*. *Prevotella* sp., *Porphyromonas* sp., *Prevotella melaninogenica*, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella cholerasuis* and *Salmonella typhimurium*), *Serratia* sp. (such as *Serratia marcesans* and *Serratia liquifaciens*), *Shigella* sp. (such as *Shigella dysenteriae*, *Shigella flexneri*, *Shigella boydii* and *Shigella sonnei*), *Staphylococcus* sp. (such as *Staphylococcus aureus*, *Staphylococcus epidermidis*, *Staphylococcus hemolyticus*, *Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), Spirillum minus, *Streptobacillus moniliformi*, *Treponema* sp. (such as *Treponema carateum*, *Treponema petenue*, *Treponema pallidum* and *Treponema endemicum*, *Tropheryma whippelii*, *Ureaplasma urealyticum*, *Veillonella* sp., *Vibrio* sp. (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio furnisii*), *Yersinia* sp. (such as *Yersinia enterocolitica*, *Yersinia pestis*, and *Yersinia pseudotuberculosis*) and *Xanthomonas maltophilia* among others.

In some examples, one or more pathogenic fungi are detected with the disclosed method. Examples of pathogenic fungi which could be detected with the disclosed methods include without limitation any one or more of (or any combination of) *Trichophyton rubrum*, *T. mentagrophytes*, *Epidermophyton floccosum*, *Microsporum canis*, *Pityrosporum orbiculare* (*Malassezia furfur*), *Candida* sp. (such as *Candida albicans*), *Aspergillus* sp. (such as *Aspergillus fumigatus*, *Aspergillus flavus* and *Aspergillus clavatus*), *Cryptococcus* sp. (such as *Cryptococcus neoformans*, *Cryptococcus gattii*, *Cryptococcus laurentii* and *Cryptococcus albidus*), *Histoplasma* sp. (such as *Histoplasma capsulatum*), *Pneumocystis* sp. (such as *Pneumocystis jirovecii*), and *Stachybotrys* (such as *Stachybotrys chartarum*) among others.

In some examples, one or more viruses are detected with the disclosed method. Examples of viruses which could be detected with the disclosed methods include without limitation any one or more of (or any combination of) Arenaviruses (such as Guanarito virus, Lassa virus, Junin virus, Machupo virus and Sabia), Arteriviruses, Roniviruses, Astroviruses, Bunyaviruses (such as Crimean-Congo hemorrhagic fever virus and Hantavirus), Barnaviruses, Birnaviruses, Bornaviruses (such as Borna disease virus), Bromoviruses, Caliciviruses, Chrysoviruses, Coronaviruses (such as Coronavirus and SARS), Cystoviruses, Closteroviruses, Comoviruses, Dicistroviruses, Flaviviruses (such as Yellow fever virus, West Nile virus, Hepatitis C virus, and Dengue fever virus), Filoviruses (such as Ebola virus and Marburg virus), Flexiviruses, Hepeviruses (such as Hepatitis E virus), human adenoviruses (such as human adenovirus A-F), human astroviruses, human BK polyomaviruses, human bocaviruses, human coronavirus (such as a human coronavirus HKU1, NL63, and OC43), human enteroviruses (such as human enterovirus A-D), human erythrovirus V9, human foamy viruses, human herpesviruses (such as human herpesvirus 1 (herpes simplex virus type 1), human herpesvirus 2 (herpes simplex virus type 2), human herpesvirus 3 (Varicella zoster virus), human herpesvirus 4 type 1 (Epstein-Barr virus type 1), human herpesvirus 4 type 2 (Epstein-Barr virus type 2), human herpesvirus 5 strain AD169, human herpesvirus 5 strain Merlin Strain, human herpesvirus 6A, human herpesvirus 6B, human herpesvirus 7, human herpesvirus 8 type M, human herpesvirus 8 type P and Human Cyotmegalovirus), human immunodeficiency viruses (HIV) (such as HIV 1 and HIV 2), human metapneumoviruses, human papillomaviruses (such as human papillomavirus-1, human papillomavirus-18, human papillomavirus-2, human papillomavirus-54, human papillomavirus-61, human papillomavirus-cand90, human papillomavirus RTRX7, human papillomavirus type 10, human papillomavirus type 101, human papillomavirus type 103, human papillomavirus type 107, human papillomavirus type 16, human papillomavirus type 24, human papillomavirus type 26, human papillomavirus type 32, human papillomavirus type 34, human papillomavirus type 4, human papillomavirus type 41, human papillomavirus type 48, human papillomavirus type 49, human papillomavirus type 5, human papillomavirus type 50, human papillomavirus type 53, human papillomavirus type 60, human papillomavirus type 63, human papillomavirus type 6b, human papillomavirus type 7, human papillomavirus type 71, human papillomavirus type 9, human papillomavirus type 92, and human papillomavirus type 96), human parainfluenza viruses (such as human parainfluenza virus 1-3), human parechoviruses, human parvoviruses (such as human parvovirus 4 and human parvovirus B19), human respiratory syncytial viruses, human rhinoviruses (such as human rhinovirus A and human rhinovirus B), human spumaretroviruses, human T-lymphotropic viruses (such as human T-lymphotropic virus 1 and human T-lymphotropic virus 2), Human polyoma viruses, Hypoviruses, Leviviruses, Luteoviruses, Lymphocytic choriomeningitis viruses (LCM), Marnaviruses, Narnaviruses, Nidovirales, Nodaviruses, Orthomyxoviruses (such as Influenza viruses), Partitiviruses, Paramyxoviruses (such as Measles virus and Mumps virus), Picornaviruses (such as Poliovirus, the common cold virus, and Hepatitis A virus), Potyviruses, Poxviruses (such as Variola and Cowpox), Sequiviruses, Reoviruses (such as Rotavirus), Rhabdoviruses (such as Rabies virus), Rhabdoviruses (such as Vesicular stomatitis virus, Tetraviruses, Togaviruses (such as Rubella virus and Ross River virus), Tombusviruses, Totiviruses, Tymoviruses, Noroviruses, bovine herpesviruses including Bovine Herpesvirus (BHV) and malignant catarrhal fever virus (MCFV), among others.

Exemplary parasites that can be identified with the disclosed methods herein include, but are not limited to, Malaria (*Plasmodium falciparum, P. vivax, P. malariae*), Schistosomes, Trypanosomes, *Leishmania*, Filarial nematodes, Trichomoniasis, Sarcosporidiasis, *Taenia* (*T. saginata, T. solium*), *Leishmania, Toxoplasma gondii,* Trichinelosis (*Trichinella spiralis*) and/or Coccidiosis (*Eimeria* species).

In some examples, a diabetic foot ulcer is identified by detecting an organism in one or more of the following genus: *Acinetobacter, Corynebacterium, Enterococcus*, and/or *Pseudomonas.*

In some examples, a diabetic foot ulcer is identified by detecting one or more of the organisms: *Acinetobacter baumannii-calcoaceticus, Corynebacterium auri, Corynebacterium* ssp., *Corynebacterium striatum, Corynebacterium striatum/amycolatum, Enterococcus faecalis*, and/or *Pseudomonas aeruginosa.*

In one example, a diabetic foot ulcer is identified by detecting one or more of the following organisms: *Acinetobacter baumannii-calcoaceticus Staphylococcus aureus, Acinetobacter baumannii-calcoaceticus Staphylococcus epidermidis, Corynebacterium auris Staphylococcus haemolyticus, Corynebacterium* spp. *Staphylococcus aureus, Corynebacterium* spp. *Staphylococcus* spp., *Corynebacterium striatum Staphylococcus aureus, Corynebacterium striatum/amycolatum Staphylococcus aureus, Corynebacterium striatum/amycolatum Staphylococcus caprae, Corynebacterium striatum/amycolatum Staphylococcus haemolyticus, Enterococcus faecalis Corynebacterium macginleyi, Enterococcus faecalis Corynebacterium striatum, Enterococcus faecalis Staphylococcus aureus, Enterococcus faecalis Staphylococcus capitis, Enterococcus faecalis Staphylococcus epidermidis, Enterococcus faecalis Staphylococcus hominis, Enterococcus faecalis Staphylococcus* sp., *Pseudomonas aeruginosa Enterococcus faecalis* and/or *Pseudomonas aeruginosa Enterococcus faecium.* ii. Molecular analysis of Sample

An exemplary molecular analysis of a biological sample is illustrated in FIG. 2. In some examples, molecular analysis of the sample includes obtaining a biological sample, such as a wound sample, from the subject. Biological samples include all clinical samples useful for identifying a bacterial infection in a subject, including, but not limited to, cells, tissues, and bodily fluids (such as blood or saliva); biopsied or surgically removed tissue, including tissues that are, for example, unfixed, frozen, fixed in formalin and/or embedded in paraffin; tears; skin scrapes; or surface washings. In a particular example, a sample includes cells collected by using a sterile swab or by a surface rinse. In some examples, a sample including nucleic acids is obtained from the subject's wound which is suspected of being infected by bacteria by a sterile swab. In some examples, the subject is displaying one or more signs or symptoms of a bacterial infection, such as inflammation or swelling, redness, presence of pus, increased surface temperature of the wound site, lack-of or delayed wound healing. In some examples, a biological sample is obtained by using the same technique used for obtaining samples for standard culture based diagnosis in a microbiology laboratory (e.g., a cotton swab).

In some examples, molecular analysis of a sample, such a wound sample, includes isolating total DNA from the sample (Step 1 of FIG. 2). Total DNA may be isolated by methods disclosed herein as well as those known to those of ordinary skill in the art, including by use of commercially available kits such as the Qiagen EZ1 DSP Virus Kit or DNeasy blood and tissue kit. Regardless of the DNA isolation method used, the resulting DNA sample is to be free of contaminants known to inhibit molecular biology procedures, (e.g., hemoglobin, Guanidine Isothiocyanate, phenol) and suspended in an appropriate buffer (e.g., Tris-EDTA buffer). In some examples, DNA is isolated within 24 hours of sample collection and stored at 4° C.

In some examples, the molecular analysis of a sample, such as a wound sample, includes removal of human DNA (Step 2 of FIG. 2), as the diagnosis and prognosis is dependent only on analysis of bacterial DNA. Human DNA may be removed from the DNA sample by methods known to those of ordinary skill in the art including those provided herein, including use of commercially available kits (e.g., NEBNext Microbiome DNA Enrichment kit).

In some examples, the molecular analysis of a sample, such as a wound sample includes preparing bacterial DNA for sequencing by fragmenting the bacterial DNA to the appropriate length for the sequencing platform to be employed (Step 3 of FIG. 2). DNA Fragmentation can be performed by methods known to those of skill in the art including enzymatic or physical methods (e.g., Ion Torrent Xpress fragment library kit or sonication on a Corvaris instrument using Adaptive Focused Acoustics technology). The methods disclosed herein are not dependent upon a particular sequencing technology. The user needs to make appropriate DNA fragment size choices for the intended downstream sequencing platform according to manufacturers' protocols. For example, Ion Torrent sequencing technology currently requires targeting a fragment size of up to 400 base pairs. Following fragmentation the bacterial DNA is size selected or purified depending on the fragmentation method. The DNA is properly sized (by length in base pairs) for the appropriate technology.

In some examples, the molecular analysis of a sample, such as a wound sample, includes sample indexing, adaptor ligation and library normalization (Step 4 in FIG. 2). Sample indexing ("barcoding") allows multiple samples to be run simultaneously taking full advantage of the high-throughput nature of current sequencing platforms. Adapter ligation is sequencing platform specific and standard to manufacturers' protocols. At this step, bacterial DNA fragments have the platform-specific end sequences necessary for sequencing along with index sequences that allow for de-convolution of sequence data by sample. Lastly, for successful sequencing, libraries are at platform specific concentrations of DNA. Libraries typically require amplification or dilution to achieve the required DNA concentration. The DNA concentration in the library can be determined by quantitative real-time PCR using platform specific manufacturer protocols. The sequencing library represents the fragments of DNA that make up the genome of the bacteria present in the patient sample. These are the molecules whose sequence is determined to generate reads that can be used for k-mer generation and subsequent analyses.

In some examples, the molecular analysis of a sample, such as a wound sample, includes performing whole metagenome sequence analysis to sequence the entire wound microbiome of the sample provided (Step 5 of FIG. 2). For example, nucleotide sequences of individual molecules are determined in a platform specific manner to produce raw data. Raw data is converted to nucleotide sequencing information for each molecule in the library in a platform-specific manner. The resulting products are whole metagenome "reads." At this point, the DNA of the bacteria has been converted to binary computer information represented in a "BAM file" that can be processed to determine information about the clinically important sample composition. BAM files are sequencing platform independent and ready for bioinformatics analysis.

iii. Data Preparation

An exemplary method of data preparation is illustrated in FIG. 3. In some examples, data preparation includes performing sequence quality control. In some examples, the resulting BAM file of reads from the molecular analysis is subjected to quality trimming, length filtering, sequencing adapter removal and binning of reads by molecular barcode. In particular, the reads that represent the DNA sequence are quality controlled to remove the platform specific adapters, clonal reads due to PCR amplification, and platform-specific sequence errors and filtered to achieve an acceptable error rate (Step 7 in FIG. 3).

In some examples, following quality control and trimming, reads that are less than two standard deviations from the mean length are discarded. Due to the high throughput of next generation sequencing, samples can be multiplexed within a single run. The indexing is achieved by the addition of a molecular bar-code consisting of sample specific sequence added to the sequencing adapters during library preparation. Following quality control, sequences are de-convoluted to create sample specific reads by analyzing the molecular bar-code at the start of each reads and binning it accordingly. At this stage, reads still contain the molecular barcodes and sequence adapters used to generate them. This sequence is not part of the bacterial genome and is to be removed before diagnosis or clinical prognosis analysis. Adapters can be removed using methods known to those of skill in the art that have been standardized to account for read errors, chimeric reads, reverse complement reads, and fragmented adapters. The resulting quality controlled sequence reads with acceptable and known error rate (e.g., phred quality score of 20 or higher at each base in the read), are the appropriate length, and contain only biologically derived sequence. The end result of the quality filtering steps are reads representing biological information free of technical errors from the sequencing process.

In some examples, data preparation includes removal of human sequence reads (Step 8 of FIG. 3). The physical removal of patient-derived DNA during sequencing library preparation is not 100% efficient. Therefore some of the reads will be derived from patient sequence and are irrelevant with respect to diagnosis or prognosis. In addition, the patient-derived reads could lead to privacy issues through inadvertent analysis of the genetic content of the patient's genome. Therefore, in some examples, the final step of quality control is in silico removal of reads derived from human DNA. For example, human sequence reads are identified by creating an array, such as a suffix array, of the reference human genome (e.g., hg19) and comparing the k-mers derived from the sample reads to a human k-mer array, such as a human k-mer suffix array, and discarding those reads with matching sequence to the reference genome from further analysis. The use of an array, such as a suffix array, and k-mers is advantageous in that it greatly speeds up computation time (discussed in more detail below). Following removal of human sequence reads, bacteria-specific sequence reads are provided. At this stage, remaining reads are high quality, appropriate length, and of bacterial origin. This represents the raw starting material for computational analyses of clinical importance (e.g. diagnosis and/or prognosis).

In some examples, data preparation includes decomposing reads into a k-mer array, such as a k-mer suffix array, thereby creating a set of sample derived k-mers (Step 9 of FIG. 3). For example, reads from the patient sample are broken into k-mers of approximately 20 bases to be compared to a suffix array of k-mers. The k-mer size can range from 20-100 bases, and is set by examining the uniqueness ratio in the dataset (Kurtz et al., (2008) *BMC Genomics* 9:517, which is hereby incorporated by reference in its entirety) the k-mer value is chosen by finding the inflection point where the k-mer hits move from "random" to representative of the sequence content. In the case of diagnosis, k-mers in the suffix array are derived from the genomic sequence of known bacteria. In the case of prognosis, the k-mer suffix array must contain k-mers derived from sequencing similar patient samples for which the clinical outcome is known (e.g., healed versus chronic wound).

As compared to other approaches that either attempt to assemble putative bacterial genomes from the metagenomic data at this step or attempt to compare samples at the read level, the methods disclosed herein "deconstruct" the reads (typically of 100-600 base pairs in length) into k-mers of approximately 20 base pairs in length (ranging between 20-100 bases). This method avoids the complex problems that arise from attempting to assemble genomes, problems that are exacerbated by the likely presence of multiple independent genomes in poly-microbial samples and the low coverage anticipated for each genome. In the case of approaches that do not attempt genome assembly, but use read to read pairwise comparison (e.g., BLAST or clustering methods such as cdhit or usearch), there is no computationally efficient way to solve the problem, leading to even simple cases becoming intractable given finite computational resources. A k-mer-based approach utilizing arrays, such a suffix array, offers a new method for dealing with the computational complexity of modern sequence datasets. Specifically, in one sample dataset, the k-mer approach was 57× faster than an all-versus-all BLAST comparison of the same dataset (Hurwitz, et al., *PNAS* 111.29 (2014): 10714-10719 which is hereby incorporated by reference in its entirety). While, other scalable heuristic clustering algorithms such as usearch and cdhit are comparable in compute time to the k-mer approach, these methods cause loss of abundance data, given that the fast heuristics only find the top few hits. Thus, the k-mer method provides comparable run times but preserves read abundances and uses the entire metagenome dataset for analysis. Therefore, the problem becomes solvable in the time frame of clinical diagnosis and the resulting dataset is comprehensive. Moreover this technique can be extended to perform fast k-mer indexing in big data architectures like Hadoop using algorithms such as Map Reduce.

iv. Patient Diagnosis

Figure 4:
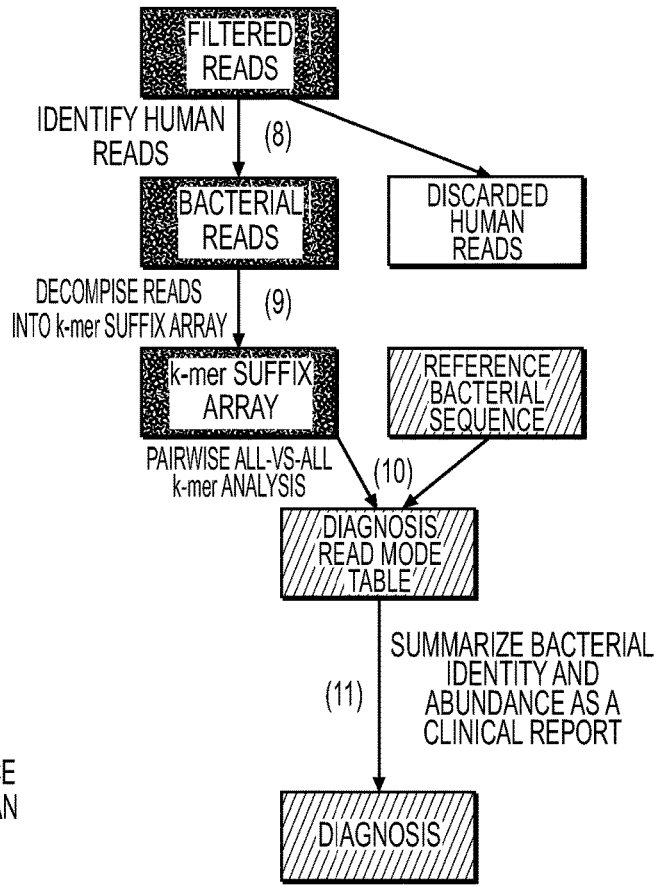
FIG. 4 is a detailed schematic of patient diagnosis performed in an exemplary method for identifying bacterial infections.

An exemplary method of patient diagnosis is illustrated in FIG. 4. In some examples, patient diagnosis includes creating a read mode table (Step 10 of FIG. 4) by comparing the k-mers derived from each sample read to the k-mer array, such as the k-mer suffix array, from known bacterial reference sequences. A count is returned of how many times the k-mer appeared in any other sample. This is a Pairwise all-versus-all problem made computationally possible by the use of short k-mers and arrays, such suffix arrays. Again, in the case of diagnosis, the array, such as a suffix array, is derived from reads of reference samples of known identity. In the case of prognosis (as discussed in detail below), the array, such as the suffix array, is derived from reads of other patient samples of known clinical outcome. The resulting counts for each k-mer comprising a sample read are analyzed to derive a mode of the reads' frequency for each pairwise comparison.

Prior to calculating the mode of each sample read from the k-mer abundance information, abundance values that are greater than two standard deviations from the mean of all k-mers from a particular read are removed. This prevents k-mers with outlier frequencies (e.g., repetitive elements, conserved protein domains) from skewing the read's mode. Using the mode of the k-mer frequency for all k-mers in a read allows one to represent the prevalence of that read in other samples. This prevalence reflects the proportion of the genome from which that read was derived and therefore allows not only the species present in the sample to be identified, but their relative proportions. In some examples, during creation of the read abundance matrix, the number of reads used from the sample(s) and references are adjusted to the minimum common denominator to prevent skewing of the relative abundances. This preserves the ability to estimate relative proportions of each genome to the total using statistical methods. The abundance value for k-mers found only infrequently in a comparison sample is set to 0 as if the k-mer was not found at all. This step keeps the mode at zero for reads that are derived from sequencing error, technical errors in library preparation (e.g., chimeras), etc. These reads are referred to as "quantum" reads, in that they will appear and disappear in technical replicates of the same sample. Failure to remove quantum reads skews conclusions derived from the sample read abundance matrix.

In some examples, diagnosing a subject includes summarizing a read mode table into a clinical report. In the case of diagnosis, the read mode table can be summarized into a simple table of species found in the sample along with their relative proportion in the sample with additional flags indicating the presence of antibiotic resistance genes.

In some examples, diagnosing a subject includes providing the results, findings, diagnoses, predictions and/or treatment recommendations to the subject. For example, the results, findings, diagnoses, predictions and/or treatment recommendations can be recorded and communicated to technicians, physicians and/or patients or clients. In certain embodiments, computers will be used to communicate such information to interested parties, such as, clients, patients and/or the attending physicians.

In some embodiments, once a subject's bacterial sequences are identified, an indication of that identity can be displayed and/or conveyed to a clinician, caregiver or a non-clinical provider, including the client/subject. For example, the results of the test are provided to a user (such as a clinician or other health care worker, laboratory personnel, or patient) in a perceivable output that provides information about the results of the method. In some examples, the output is a paper output (for example, a written or printed output), a display on a screen, a graphical output (for example, a graph, chart, or other diagram), or an audible output.

In other examples, the output is a numerical value, such as an amount of a particular set of sequence in the sample as compared to a control. In additional examples, the output is a graphical representation, for example, a graph that indicates the value (such as amount or relative amount) of the particular bacteria in the sample from the subject on a standard curve. In a particular example, the output (such as a graphical output) shows or provides a cut-off value or level that indicates the presence of a bacterial infection. In some examples, the output is communicated to the user, for example by providing an output via physical, audible, or electronic means (for example by mail, telephone, facsimile transmission, email, or communication to an electronic medical record).

The output can provide quantitative information (for example, an amount of an molecule in a test sample compared to a control sample or value) or can provide qualitative information (moderate to severe bacterial infection caused by a particular bacteria indicated). In additional examples, the output can provide qualitative information regarding the relative amount of a particular bacteria in the sample, such as identifying presence of an increase relative to a control, a decrease relative to a control, or no change relative to a control.

In some examples, the output is accompanied by guidelines for interpreting the data, for example, numerical or other limits that indicate the presence or absence of a particular bacterial disorder/condition. The indicia in the output can, for example, include normal or abnormal ranges or a cutoff, which the recipient of the output may then use to interpret the results, for example, to arrive at a diagnosis, prognosis, susceptibility towards or treatment plan. In some examples, the findings are provided in a single page diagnostic report (e.g., PDF file) for the healthcare provider to use in clinical decision making.

Based on the findings, the therapy or protocol administered to a subject can be started, modified not started or re-started (in the case of monitoring for a reoccurrence of a particular condition/disorder). In some examples, recommendations of what treatment to provide are provided either in verbal or written communication. In some examples, the recommendations are provided to the individual via a computer or in written format and accompany the diagnostic report. For example, a subject may request their diagnostic report and suggested treatment protocols be provided to them via electronic means, such as by email.

In some examples, the diagnostic report may include determination of other clinical or non-clinical information.

In certain embodiments, the communication containing the diagnostic results and/or treatment recommendations or protocols based on the results, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, performing the comparisons, and/or communicating of assay results, diagnoses or recommendations, may be carried out in diverse (e.g., foreign) jurisdictions. In additional embodiments, the treatment, dose or dosing regimen is modified based on the information obtained using the methods disclosed herein.

The subject can be monitored while undergoing treatment using the methods described herein in order to assess the efficacy of the treatment or protocol. In this manner, the length of time or the amount given to the subject can be modified based on the results obtained using the methods disclosed herein. The subject can also be monitored after the treatment using the methods described herein to monitor for relapse and thus, the effectiveness of the given treatment. In this manner, whether to resume treatment can be decided based on the results obtained using the methods disclosed herein. In some examples, this monitoring is performed by a clinical healthcare provider. In other examples, this monitoring is performed by a non-clinical provider and can include self-monitoring or monitoring by a weight consultant.

v. Clinical Prognosis

An exemplary method of clinical prognosis is illustrated in FIG. 5. In some examples, clinical prognosis includes creating a prognosis read mode table (Step 12 of FIG. 5) by comparing k-mers from patient derived reads to prior clinical samples for which outcome is known. In some examples, the read mode table is summarized into a sample read abundance matrix (Step 13 of FIG. 5). This matrix is the raw data from which Bayesian social network analysis is performed (Step 14 of FIG. 5). In some examples, the sample read abundance matrix is subsampled many times using a Bayesian social network analysis until convergence is reached. Simultaneously, linear regression is performed on metadata derived from the diagnosis in step 10 of FIG. 4 and on potentially significant patient data (e.g., risk factors or a clinical data). In one particular example, the read abundance matrix is subsampled many times with the read abundance used to calculate multi-dimensional distance vectors and simultaneously perform statistical analysis of the contribution of metadata variables to the vectors. It is contemplated that the metadata variables can include various type of information including, but not limited to, patient factors (e.g., weight, age, sex, blood glucose, etc.) as well as the content of the diagnosis from Step 11 of FIG. 4. The results of the analysis can be a visual representation of the patient sample relative to other patient samples of known outcome along with statistically derived p-value values for provided metadata. In some examples, the method includes using Bayesian network analysis and not principal component analysis. By using Bayesian network analysis, as opposed to principal component analysis, reads that drive the statistically significant metadata variables can be extracted from the results, allowing the identification of mechanistic explanations for clinical outcome (Step 15 of FIG. 5) and discovery of novel biomarkers (Step 16 of FIG. 5). Clinical outcome may be determined by analyzing statistically the probabilistic distance a patient sample is from other samples of known outcomes and reporting such as a risk (e.g., risk the patient's wound will be chronic). For example, a deliverable single page diagnostic report (e.g., PDF file) may be generated for the physician to use in clinical decision making indicating whether a patient sample belongs to a particular prior grouping (healed versus chronic wound). Additional formats may be utilized to provide the results including those discussed herein as well as those known to those of ordinary skill in the art.

By using Bayesian network analysis the sequence reads that drive prognosis and diagnosis are extractable from the total data. These reads can be translated in silico into putative protein sequence and analyzed against protein motif databases to identify protein functions that correlate significantly with clinical information (e.g., protease or beta-lactamase activity correlating with tissue invasion or antibiotic resistance). In addition, the sequence reads could provide novel biomarkers for the development of rapid diagnostic assays. Thus the disclosed methods can be used to identify protein function as well as novel biomarkers.

vi. Providing a Treatment/Protocol to a Subject

In some embodiments, the method further includes providing an appropriate therapy or protocol for the subject after reviewing the diagnostic and/or prognostic report. For example, a subject diagnosed with a particular bacterial infection can be provided a particular therapy. In some examples, the therapy includes administering an agent to alter one or more signs or symptoms associated with the identified bacterial disorder/condition. The treatment/protocol can be performed multiple times for optimal results. In one embodiment, the treatment is performed twice a day. In another embodiment, the treatment is performed daily. In other embodiments, the recommendation/treatment is performed weekly. In another embodiment, the treatment is performed monthly. In another embodiment, the treatment is performed at least once every one to two days. In another embodiment, the treatment is performed at least once every one to two weeks.

It is contemplated that the desired treatments or protocols may be administered via any means known to one of skill in the art, including oral, topical, or systemic administration. In some examples, a composition is administered to the subject orally, such as in a capsule or tablet. It is contemplated that one or more compositions can be administered via multiple routes as the same or different time period depending upon the disorders/conditions being treated. The percentage of improvement can be, for example, at least about a 5%, such as at least about 10%, at least a 15%, at least a 20%, at least about 30%, at least about 40%, at least about 50%, at least about 60%, at least about 70%, at least about 80%, at least about 90% or at least about 100% change compared to the baseline score prior to treatment with one or more bacterial altering/controlling agents. The improvement can be measured by both subjective and objective methods, and can be quantified using a subjective scoring or a panel scoring, amongst other methods.

IV. Exemplary Computing Environment

Figure 6:
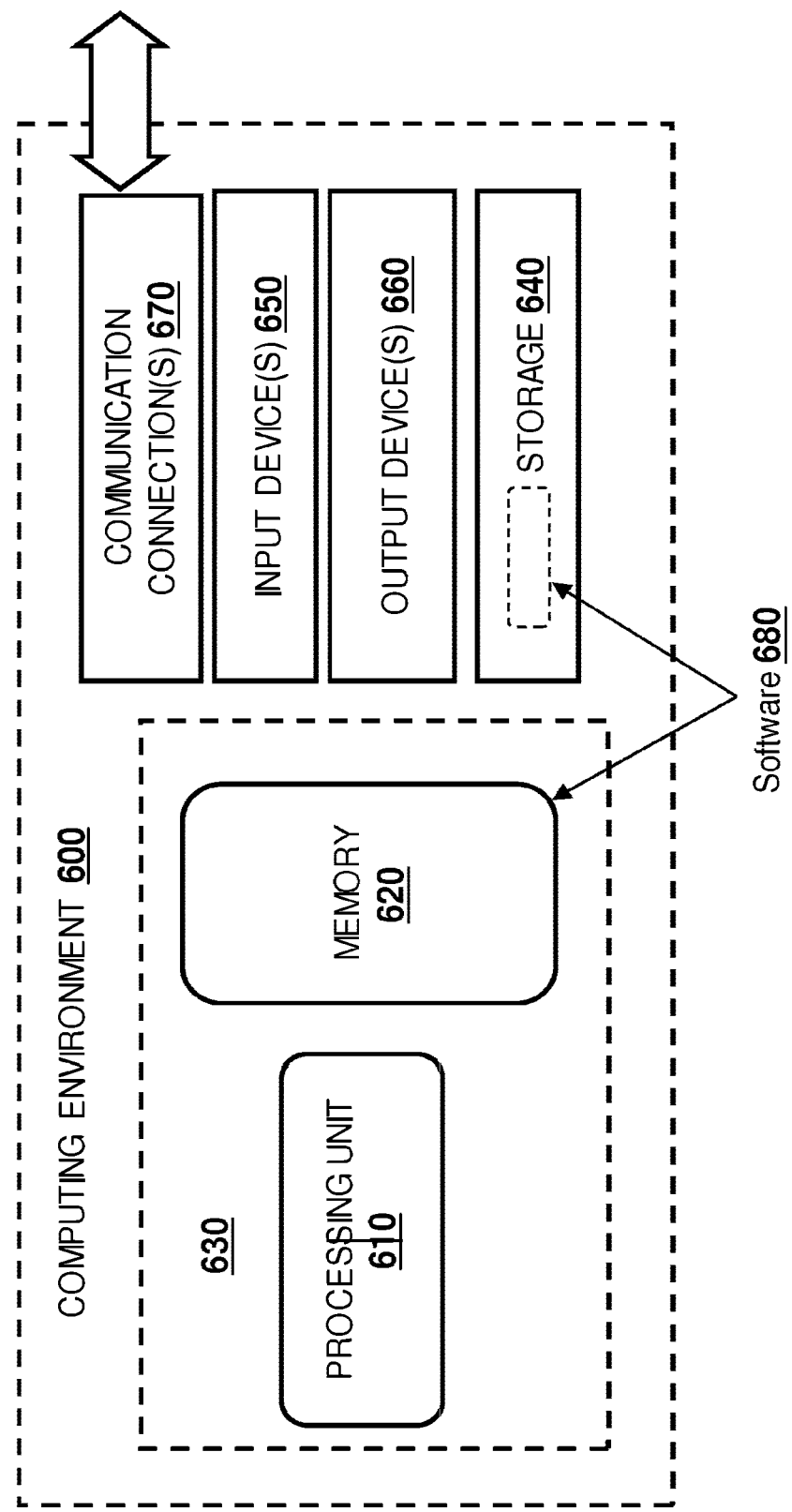
FIG. 6 is a system illustrating a generalized computer network arrangement, in one embodiment of the present technique.

One or more of the above-described techniques may be implemented in or involve one or more computer systems. FIG. 6 illustrates a generalized example of a computing environment 600. The computing environment 600 is not intended to suggest any limitation as to scope of use or functionality of described embodiments.

With reference to FIG. 6, the computing environment 600 includes at least one processing unit 610 and memory 620. In FIG. 6, this basic configuration 630 is included within a dashed line. The processing unit 610 executes computer-executable instructions and may be a real or a virtual processor. In a multi-processing system, multiple processing units execute computer-executable instructions to increase processing power. The memory 620 may be volatile memory (e.g., registers, cache, RAM), non-volatile memory (e.g., ROM, EEPROM, flash memory, etc.), or some combination of the two. In some embodiments, the memory 620 stores software 680 implementing described techniques.

A computing environment may have additional features. For example, the computing environment 600 includes storage 640, one or more input devices 650, one or more output devices 660, and one or more communication connections 670. An interconnection mechanism (not shown) such as a bus, controller, or network interconnects the components of the computing environment 600. Typically, operating system software (not shown) provides an operating environment for other software executing in the computing environment 600, and coordinates activities of the components of the computing environment 600.

The storage 640 may be removable or non-removable, and includes magnetic disks, magnetic tapes or cassettes, CD-ROMs, CD-RWs, DVDs, or any other medium which may be used to store information and which may be accessed within the computing environment 600. In some embodiments, the storage 640 stores instructions for the software 680.

The input device(s) 650 may be a touch input device such as a keyboard, mouse, pen, trackball, touch screen, or game controller, a voice input device, a scanning device, a digital camera, or another device that provides input to the computing environment 600. The output device(s) 660 may be a display, printer, speaker, or another device that provides output from the computing environment 600.

The communication connection(s) 670 enable communication over a communication medium to another computing entity. The communication medium conveys information such as computer-executable instructions, audio or video information, or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Implementations may be described in the general context of computer-readable media. Computer-readable media are any available media that may be accessed within a computing environment. By way of example, and not limitation, within the computing environment 600, computer-readable media include memory 620, storage 640, communication media, and combinations of any of the above.

V. Non-Transitory Computer-Readable Media

Any of the computer-readable media herein can be non-transitory (e.g., volatile or non-volatile memory, magnetic storage, optical storage, or the like).

VI. Storing in Computer-Readable Media

Any of the storing actions described herein can be implemented by storing in one or more computer-readable media (e.g., computer-readable storage media or other tangible media). Any of the things described as stored can be stored in one or more computer-readable media (e.g., computer-readable storage media or other tangible media).

VII. Methods in Computer-Readable Media

Any of the methods described herein can be implemented by computer-executable instructions in (e.g., encoded on) one or more computer-readable media (e.g., computer-readable storage media or other tangible media). Such instructions can cause a computer to perform the method. The technologies described herein can be implemented in a variety of programming languages.

VIII. Methods in Computer-Readable Storage Devices

Any of the methods described herein can be implemented by computer-executable instructions stored in one or more computer-readable storage devices (e.g., memory, magnetic storage, optical storage, or the like). Such instructions can cause a computer to perform the method.

Having described and illustrated the principles of our invention with reference to described embodiments, it will be recognized that the described embodiments may be modified in arrangement and detail without departing from such principles. It should be understood that the programs, processes, or methods described herein are not related or limited to any particular type of computing environment, unless indicated otherwise. Various types of general purpose or specialized computing environments may be used with or perform operations in accordance with the teachings described herein. Elements of the described embodiments shown in software may be implemented in hardware and vice versa.

EXAMPLES

Example 1

Figures 7C, 7D:
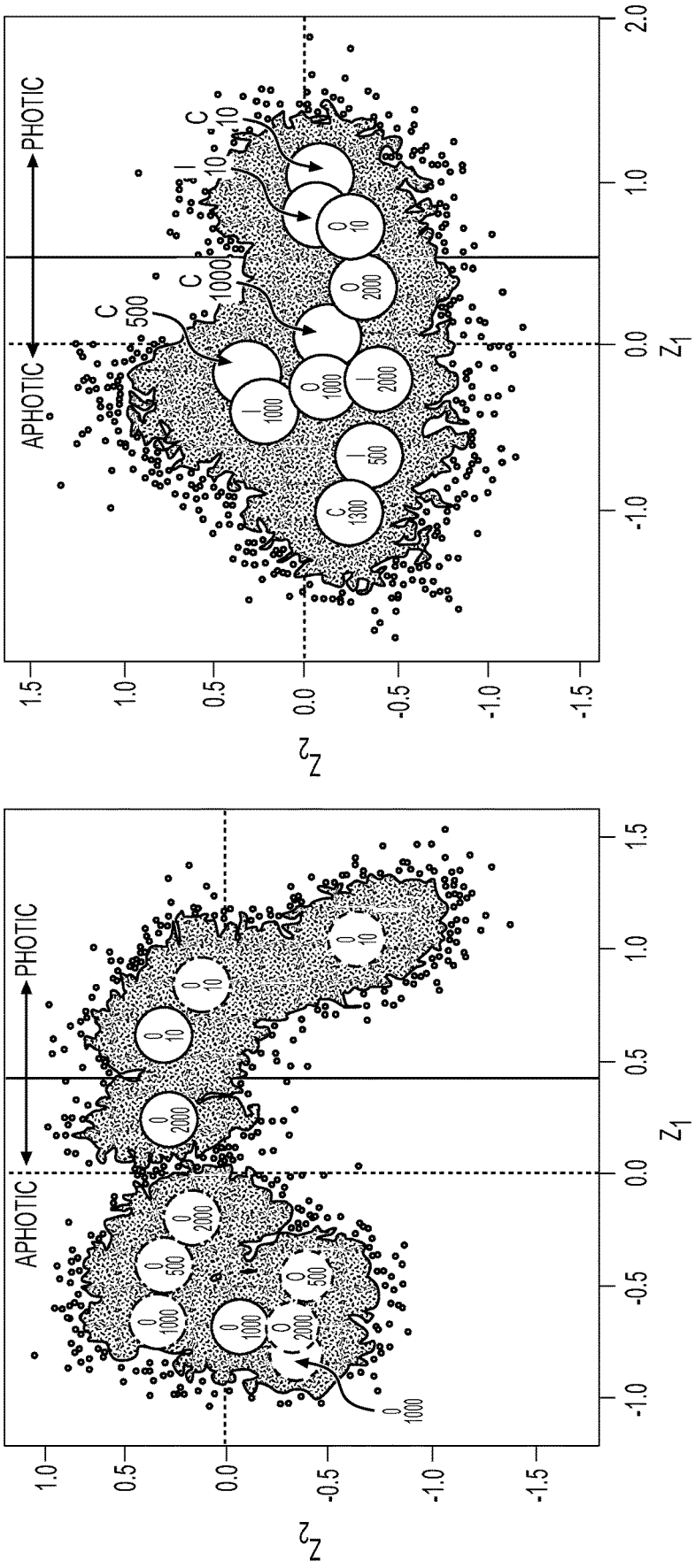

The disclosed method has been successfully applied to viral metagenomes (viromes) from the Pacific Ocean (Hurwitz, et al., PNAS 111.29 (2014): 10714-10719, which is hereby incorporated by reference in its entirety). Unlike bacteria, viruses lack conserved gene markers like the 16s ribosomal RNA gene which limits our ability to infer their abundance and diversity in a given environment. Further, typically more than 90% of reads are unknown when compared to reference sequence databases. Thus, a new strategy to compare sets of entire metagenomes using a fast pairwise k-mer analysis and social network analysis (SNA) was designed. As part of the SNA, a regression analysis was performed to assess the significance of metadata factors associated with viromes (i.e. season, proximity to shore, depth, geographic region). The result was a network of viromes that are visually represented based on their sequence similarity to one-another (FIGS. 7A-7D) and a robust statistical framework to assess which factors (i.e. metadata) significantly predict the network structure. Further, the model accounts for dependency among factors and can be used with multi-dimensional datasets. This analysis produced the first visualization of entire viromes (32 viromes with 100% of 6M reads included; FIG. 7A) and quantified the amount of overlap in sequence composition between sunlit and dark ocean waters (FIG. 7B). Broad patterns were observed such as significant differences between viral communities in sunlit (photic) versus dark (aphotic) ocean waters (FIGS. 7A, 7C, 7D), and differences between seasons (FIG. 7C). This analysis also showed that long held beliefs that viral communities were significantly different from coastal to open ocean was not true, and instead communities were homogenized by current patterns in the surface and deep waters (FIG. 7D). Thus, these network analyses enabled the testing of existing hypotheses and generate new theories about ecological drivers of viral community structure in ways that are computationally scalable and applicable to diverse sequence-based large-scale comparative studies.

Materials and Methods

Dataset.

The 32-virome POV dataset (Hurwitz & Sullivan, PLoS ONE, 8(2):e57355 (2013)) was examined to identify patterns of sequence similarity in viromes and determine the relationship between these patterns and depth, season, proximity to shore, geographic distance, and oxygen concentration. This dataset is a recently available public resource that leverages well-characterized sample-to-sequence preparation methods to generate quantitative viromes (Hurwitz, et al., Environ Microbiol, 15(5):1428-1440 (2013), Ladau, et al., ISME J, 7(9):1669-1677 (2013)). A full description of metadata associated with each virome and methods used to prepare the viromes and perform read quality control is discussed below. One additional filtering step was applied beyond the quality control steps for the POV dataset (Hurwitz & Sullivan, PLoS ONE, 8(2):e57355 (2013)) that entailed removing reads with low abundance k-mers (k-mer=1) in their own virome that were suspected of being contaminants (Hurwitz, et al., Environ Microbiol, 15(5): 1428-1440 (2013)) and reads with high-abundance k-mers (>1,000) that are likely to be either sequencing artifacts or highly conserved protein domains that may distort the overall abundance of that read.

k-mer Analyses.

In the k-mer analysis below, suffix arrays were created using mkvtree from the vmatch package version 2.1.5 (Kurtz, et al., BMC Genomics, 9:517 (2008)) using parameters (-pl -allout -v). Reads were compared with suffix arrays using vmatch's vmerstat (-minocc 1-counts) to search for the frequency of 20-bp k-mers across the read. The k-mer size was set by examining the uniqueness ratio in the dataset (Chiu & Westveld, Stat Methodol, 17(4432):139-160 (2014)). The k-mer value of 20 was chosen given that it represented an inflection point where k-mer hits moved from random to representative of the sequence content.

Pairwise all-Vs.-all Analysis of Viromes.

High-quality reads for each virome were compared with suffix arrays from all other viromes in a pairwise fashion (compute pipeline kmercompare.tar) to achieve an all-vs.-all analysis of the viromes [virome i vs. virome j, (for i=1, ..., 32) and (for j=1, ..., 32)]. The abundance for each read (in virome i) was calculated by finding the mode k-mer value for all k-mers in that read compared with the virome j suffix array. This analysis resulted in a single abundance value (k-mer mode) for each read in virome i compared with virome j. The data were then normalized by averaging ($\bar{y}_{i,j}$) (shared read count) and ($\bar{n}_{i,j}$) (total read count) between virome i and virome j. Normalized shared read counts were used to construct a 32×32 matrix of viromes.

Network Analysis.

To model the valued (nonbinary) nondirected data above, the latent space approach outlined in Eq. 1 (Hoff, J Am Stat Assoc, 100(469):286-295 (2005), Chiu & Westveld, Proc Natl Acad Sci USA, 108(38):15881-15886 (2011), Hurwitz, et al., Genome Biol, 14(11):R123 (2013), R Core Team (2012) R: A Language and Environment for Statistical Computing (R Foundation for Statistical Computing, Vienna)) was considered. The network modeling framework, via random effects, decomposes the statistical variation in the data to account for (i) the activity level ($a_i$) of each virome i (average amount of sequence space shared across the network for each virome i) and (ii) similarity (clustering) of shared sequence amount among viromes. For i), $z'_i z_j$ is measure of distance and similarity between viromes i and j. Each virome's position ($z_i$) may be visualized in a k-dimensional latent space Z (after a Procrustes' transformation to convert into a similar grid to compare) where virome i and virome j are considered similar if they are close in that space. For ease of visualization, the case where k=2 (R Core Team (2012) R: A Language and Environment for Statistical Computing (R Foundation for Statistical Computing, Vienna) considered a 1D space) was considered.

Finally, a set of relational covariates ($x_{ij}$=1 if similar, 0 if not) was accounted for based on geographic region, season, proximity to shore, depth, and oxygen concentration values. In the case of oxygen concentration, which is a continuous value, high and low oxygen values were determined based on a cutoff of 0.06 mL/L.

$$\log(\bar{y}_{i,j}) = \alpha + \gamma \log(\bar{n}_{i,j}) + \beta' x_{ij} + a_i + a_j + z'_i z_j + \varepsilon_{ij}$$

$$i < j,$$

$$a_i \sim \text{identically distributed normal}(0, \sigma_a^2),$$

$$z_{i,1} \sim \text{identically distributed normal}(0, \sigma_{z1}^2),$$

$$z_{i,2} \sim \text{identically distributed normal}(0, \sigma_{z2}^2),$$

$$\varepsilon_{ij} \sim \text{identically distributed normal}(0, \sigma_\varepsilon^2). \quad [1]$$

To estimate the parameters in the model, a Bayesian inferential approach was considered using the R statistical software (Hoff, http://www.stat.washington.edu/hoff/Code/hoff_2005jasa. Accessed on Dec. 31, 2013) and gbme.R obtained from Chiu & Westveld, Proc Natl Acad Sci USA, 108(38):15881-15886 (2011) and Wilkinson, et al., IEEE Trans Vis Comput Graph, 18(2):321-331 (2012). For the analyses, empirical Bayes priors were considered (the default for the gbme.R). To examine the joint posterior distribution of the parameters, a Markov chain of 1,000,000 scans was constructed. The first 500,000 scans were removed for burn-in, and the chain was thinned by every 100th scan, leaving 5,000 samples.

Construction of Euler Diagrams Depicting Shared Read Content in Networks.

Using data from the pairwise k-mer analysis described above, reads were detected that were unique or shared between subsets of viromes that visually clustered in the networks using a PERL script (get_section.pl). Reads were considered exclusive if they were present (mode k-mer >2) in two or more viromes in a cluster and absent (mode k-mer <2) from viromes outside that cluster. For single virome clusters, all reads that were not shared with other viromes and present within that single virome at a k-mer abundance >2 were considered exclusive. Reads that were present in a virome just once (k-mer=1) were removed from the analysis given a higher probability of contamination (Hurwitz, et al., Environ Microbiol, 15(5):1428-1440 (2013)) per the discussion above. The results were then used to compute an Euler diagram using the venneuler function (Rattei, et al., SIMAP: the similarity matrix of proteins. Nucleic Acids Res 34(Database issue):D252-D256 (2006)) in the R statistical software (Hoff, http://www.stat.washington.edu/hoff/Code/hoff_2005jasa. Accessed on Dec. 31, 2013).

Annotating Exclusive Reads.

Exclusive reads per the method above for LineP summer photic viromes, summer aphotic viromes, winter photic viromes, and winter aphotic viromes were compared against the similarity matrix of proteins (SIMAP) released on Aug. 20, 2013 (Yamada, et al., *Nucleic Acids Res*, 39 (Web Server issue):W412-W415 (2011)) using BLASTX (De Ferrari, et al., *BMC Bioinformatics*, 13:61 (2012)) to assign function as previously described (Bench, et al., *Appl Environ Microbiol*, 73(23):7629-7641 (2007)). Briefly, these analyses were implemented using a custom data analysis pipeline written in Perl and bash shell and executed on a high-performance computer using PBSPro (blastpipeline_simap.tar). Hits were considered significant if they had an E value <0.001, and only top hits were retained. Interpro ids in the SIMAP functional annotation were mapped to EC numbers using the swissprot_kegg_proteins_ec.csv as a mapping (Altschul, et al., *Nucleic Acids Res*, 25(17):3389-3402 (1997)) (ipr_to_ec.pl). Read hit counts were normalized based on sequencing effort in the included viromes and converted into ipath2 format (create_ipath.pl) for visual representation in the ipath2 viewer (De Ferrari, et al., *BMC Bioinformatics*, 13:61 (2012)).

Supplemental Materials and Methods

Virome, Metadata, and K-mer Analysis Details. Constructing Viromes.

Viromes were constructed from 32 seawater samples in the Pacific Ocean that varied by depth, season, proximity to shore, geographic distance, and oxygen concentration (Hurwitz, et al., *Environ Microbiol*, 15(5):1428-1440 (2013), Hurwitz & Sullivan, *PLoS ONE*, 8(2):e57355 (2013)). Briefly, seawater samples were prefiltered using a 150-µm grade A glass microfiber filter to enrich for bacterial and viral-sized particles in the filtrate. The filtrate was then passed through a subsequent 0.22-µm filter to enrich for viral-sized particles only. Viral-sized particles were then concentrated from the remaining filtrate using FeCl3 precipitation and purified by DNase and CsCl. Three comparison viromes were also constructed from a single sample at Scripps Pier (SIO) using the following concentration and purification protocols: (i) tangential flow filtration (TFF) and DNase and CsCl, (ii) FeCl3 precipitation and DNase only, and (iii) FeCl3 precipitation and DNase and sucrose as previously described (Hurwitz, et al., *Environ Microbiol*, 15(5):1428-1440 (2013)). Following DNA extraction using Wizard PCR DNA Purification Resin and Minicolumns as previously described (Henn, et al., *PLoS ONE*, 5(2):e9083 (2010)), viral DNA was randomly size sheared and amplified using linker amplification (LA) as described previously (Duhaime, et al., *Environ Microbiol*, 14(9):2526-2537 (2012)) in preparation for sequencing. Samples were sequenced using GS FLX Titanium sequencing chemistry on a 454 Genome Sequencer. Multiple samples were multiplexed on a single sequencing run by adding sample specific molecular barcodes during adapter ligation in the library preparation step.

Data Preparation.

Quality Control of Reads.

Following sequencing, reads were passed through a quality filter to remove low-quality reads that were less than 2 SDs from the mean length and quality or contained an "N" anywhere in the read. To remove technical replicates, high-quality reads were then passed through cd-hit-454 (using default parameters, version 4.5.5) (Niu, et al., *BMC Bioinformatics*, 11:187 (2010)). Next, reads were binned by sample based on their molecular barcode, and the barcode and platform-specific adapter were trimmed to produce the 32 viromes used in this analysis. Custom quality filtering code was written in Perl and shell script to implement this protocol as a pipeline on a compute cluster running PBSPro (screenpipe.tar).

K-mer Analyses.

In each k-mer analysis below (both for removing contaminating reads and for pairwise all-vs.-all comparison of viromes), suffix arrays were created using mkvtree from the vmatch package version 2.1.5 (www.vmatch.de) using parameters (-pl -allout -v). Reads were compared with suffix arrays using vmatch's vmerstat (-minocc 1-counts) to search for the frequency of 20-bp k-mers across the read.

Removal of High and Low Abundance Contaminating Reads.

Figure 8:
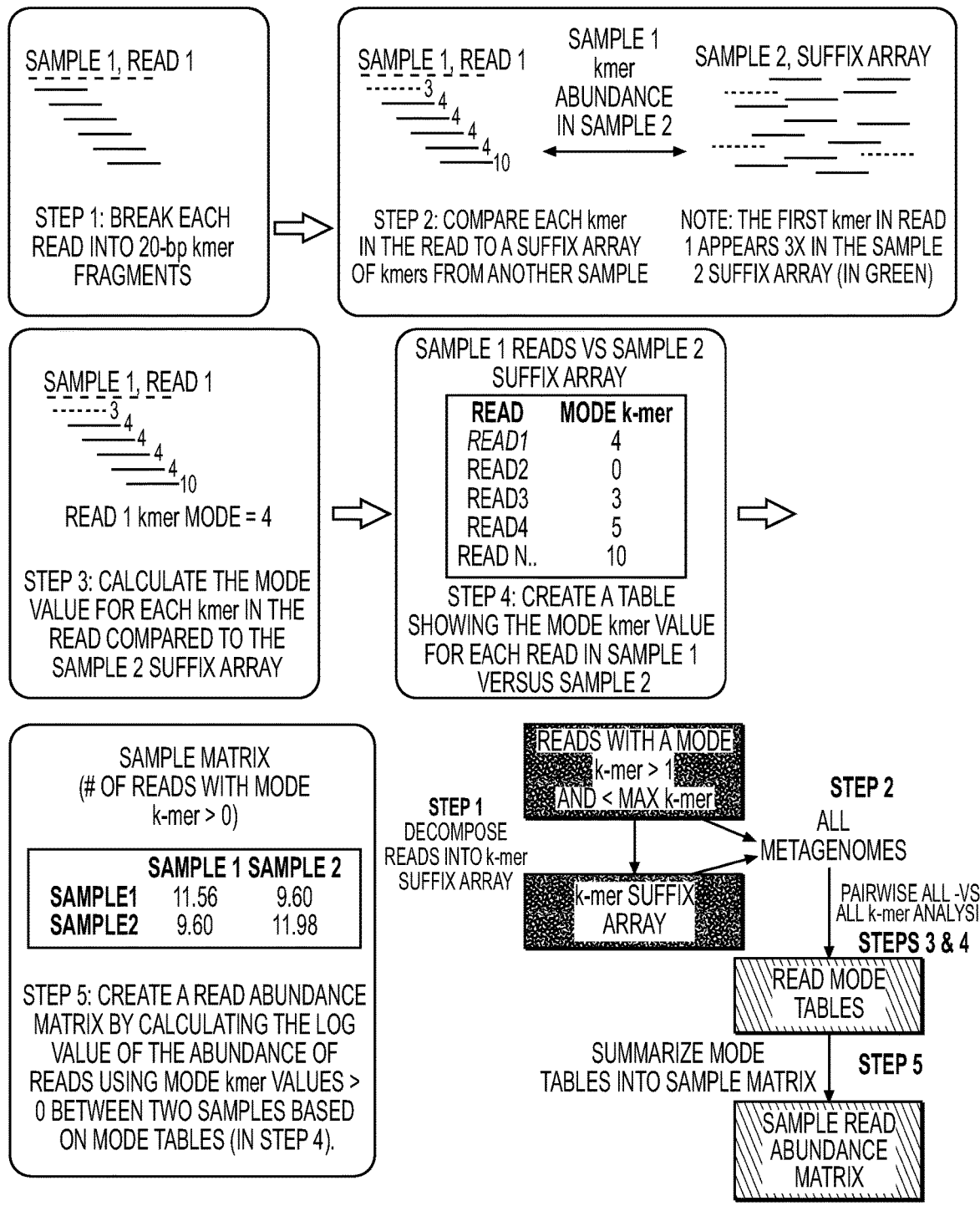
FIG. 8 is a detailed flow chart of an exemplary k-mer approach.
Figure 9:
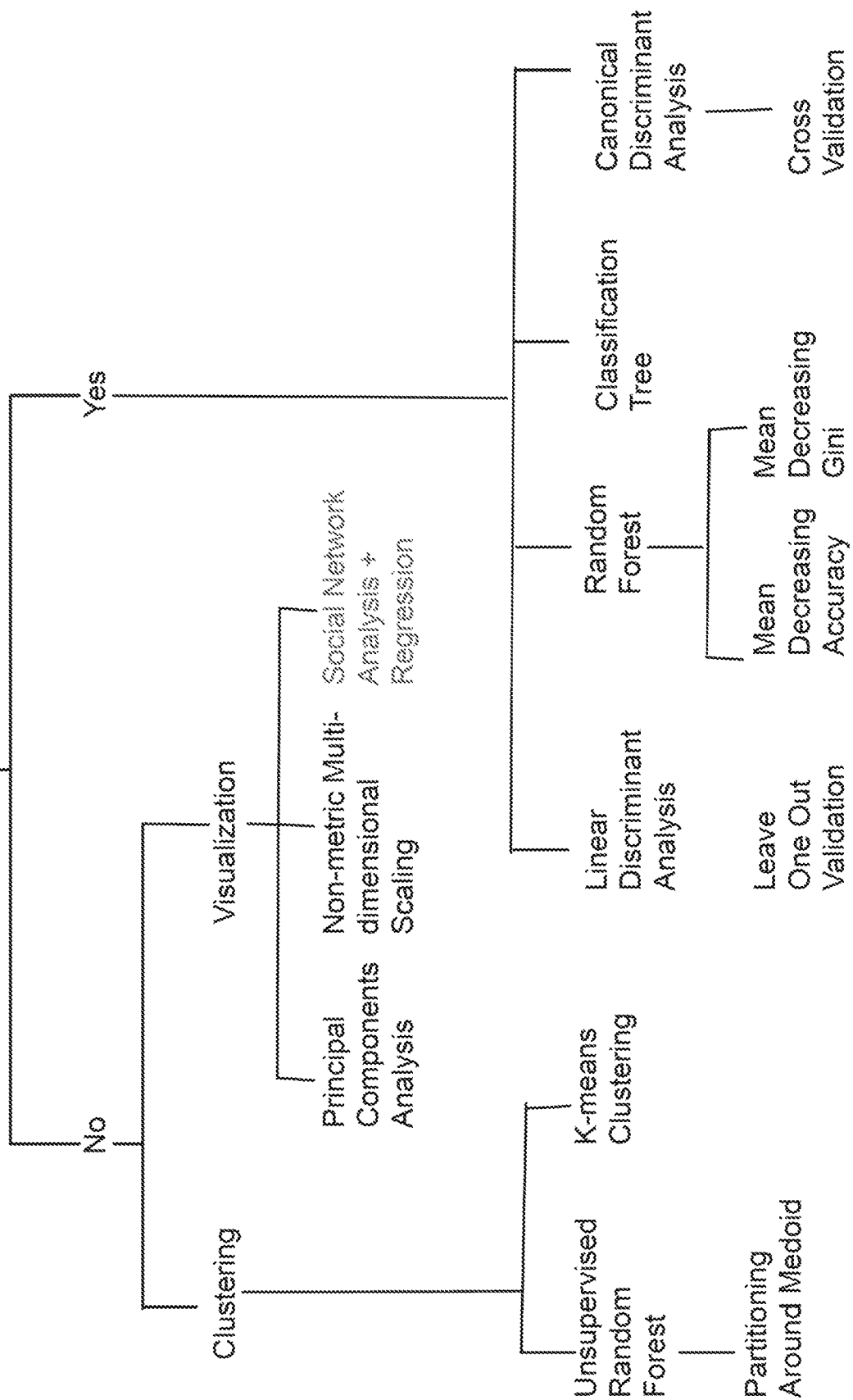
FIG. 9 is a decision tree illustrating the disclosed methods within the tree to analyze high-dimensional datasets.

To remove other potential sequencing errors, a k-mer-based approach was applied to compare reads from each virome to a suffix array from the same virome (FIG. 8). The main concept was that rare reads, wherein the mode value of k-mers in the read is <1 in the same virome (FIG. 8), are likely to be contaminants (Hurwitz, et al., *Environ Microbiol*, 15(5):1428-1440 (2013), Zhang, et al., arXiv: 1309.2975 (2013)) and therefore were removed before further analysis. Moreover, portions of the read with k-mers that appear >1,000 [more than 10× the average read coverage by contig assembly analysis (Hurwitz & Sullivan, *PLoS ONE*, 8(2):e57355 (2013))] in the suffix array for the same virome are likely to be either sequencing artifacts or highly conserved protein domains that may distort the overall abundance of that read. As a result, these high-abundance k-mers were masked out with Ns in the read and trimmed from the beginning or end of the read. Further, any reads that were less than 100 bp after masking and trimming were removed. Given this k-mer filtering approach, reads were able to be detected with aberrant k-mers (from sequencing artifact or in highly conserved protein domains) that could confound an analysis of the relative abundance of reads between metagenomes.

Pairwise all-Vs.-all Analysis of Viromes.

After reads with aberrant k-mers were removed (both low and extremely high abundance k-mers), reads for each virome were compared with suffix arrays from all other viromes in a pairwise fashion (compute pipeline kmercompare.tar) to achieve an all-vs.-all analysis of the viromes [virome i vs. virome j, for (i=1; . . . ; 32) and (for j=1; . . . ; 32)].

Data Analysis Pipeline.

Matrix of Read Counts Based on Reads with Shared k-Mers.

Following the k-mer-based pairwise analysis of viromes, read mode tables were created to capture the abundance of each read between viromes (number of times virome i read appears in virome j; FIG. 8). The abundance for each read (in virome i) was calculated by finding the mode k-mer value for all k-mers in that read compared with the virome j suffix array (FIG. 8). This analysis resulted in a single abundance value (k-mer mode) for each read in virome i compared with virome j (FIG. 8). The mode tables were then used to construct a 32×32 matrix of shared read counts ($y_{i,j}$) between pairwise combinations of viromes. Reads in virome i were considered to be shared with virome j, if the mode k-mer value for the read was >2. Each shared read in the mode table increments the total shared read ($y_{i,j}$) count for the pair of viromes by 1.

Creating Matrices of Covariates.

Matrices of relational covariates were created for each metadata type, specifically geographic region, season, proximity to shore, depth, and oxygen concentration. For each cell in the matrix comparing two viromes, if two samples have exactly the same value, then they are coded ($x_{ij}=1$) for being the same; otherwise, they are coded as ($x_{ij}=0$). In the case of oxygen concentration, which is a continuous value, high and low oxygen values were established using a cutoff of 0.06 mL/L (low oxygen values). Viromes were then coded ($x_{ij}=1$) for being the same if they were both high or low oxygen. Network analyses were performed according to the detailed methods provided later.

Runtime Analyses and Comparison with Other Methods.

Given the dramatic decrease in sequencing costs with next-generation sequencing technologies, rapid and scalable methods to analyze large-scale genomic and metagenomic datasets are fundamental. Beyond the biological conclusions outlined here, this article also offers a method for dealing with the computational complexity of modern datasets. Specifically, the k-mer method is 57× faster than an all-vs.-all blast comparison of the same dataset. Extrapolation to the scale of datasets currently being generated (80,000,000 high-quality reads on a next-generation sequencing platform), the k-mer analysis would complete in 6 h compared with 1.5 wk for an all-vs.-all blast analysis on a 32-core high performance compute cluster. Moreover, the kmer method is comparable in computing time to other scalable heuristic clustering algorithms such as usearch and cdhit (Edgar, *Bioinformatics*, 26(19):2460-2461 (2010), Huang, et al., *Bioinformatics*, 26(5):680-682 (2010)). Although run times are similar, the k-mer method uses the entire dataset to compute read abundance across metagenomes (with mode k-mer abundance reported for the read; FIG. 8), whereas such abundance data are lost with clustering methods because the fast heuristics find only the top few hits resulting in presence/absence data cdhit (Edgar, *Bioinformatics*, 26(19):2460-2461 (2010), Huang, et al., *Bioinformatics*, 26(5):680-682 (2010)). Thus, the k-mer method provides comparable run times but more comprehensive analysis of metagenomes.

Statistical Modeling Details.

Model Structure.

The relational data being modeled, in its simplest form, is a proportion $y_{i,j}/n_{i,j}$, where $y_{i,j}$ represents the number of reads in common (reading in one direction) over the total possible number of counts $n_{i,j}$ (reading in one direction). Although a natural approach to deal with these type of data are through binomial distribution, an alternative was considered by taking the natural log of the proportion within the following regression setting $$\log(y_{i,j}/n_{i,j})=\beta'x_{i,j}+\delta_{i,j}$$

$$\log(y_{i,j})-\log(n_{i,j})=\beta'x_{i,j}+\delta_{i,j}$$

$$\log(y_{i,j})=\log(n_{i,j})+\beta'x_{i,j}+\delta_{i,j}$$

where $x_{i,j}$ is a vector of covariates, and $\delta i,j$ is an error term. Moving the term $\log(n_{i,j})$ over to the right side of the regression makes that term an offset (Breitbart, et al., *Proc Natl Acad Sci USA*, 99(22):14250-14255 (2002)). However, as the data actually consist of reading in two directions and averaging those results:

$$\log(\bar{y}_{i,j})=\log(\bar{n}_{i,j})+\beta'x_{i,j}+\delta_{i,j}.$$

Finally, more generality was allowed for by not forcing the coefficient of $\log(n_{i,j})$ to be equal to 1

$$\log(\bar{y}_{i,j})=\gamma \log(\bar{n}_{i,j})+\beta'x_{i,j}+\delta_{i,j}. \quad [S1]$$

As the data are nondirected ($y_{i,j} \equiv y_{j,i}$ and $n_{i,j} \equiv n_{j,i}$) only the data for $i<j$ was considered. To accommodate the potential dependencies that arise in nondirected relational data, consider the following decomposition of $\delta_{i,j}$ into the following mean zero random effects (based on Chiu & Westveld, *Stat Methodol*, 17(4432):139-160 (2011), Gelman, et al., Bayesian Data Analysis (CRC, Boca Raton, Fla.) (2014), Hoff, et al., *J Am Stat Assoc*, 97(460):1090-1098 (2002)):

$$\bar{o}_{i,j} = a_i + a_j + z_i'z_j + \epsilon_{i,j} \quad [S2]$$

$$a_i \overset{iid}{\sim} \text{normal}(0, \sigma_a^2)$$

$$z_i \overset{iid}{\sim} \text{multivariate normal}_{k=2}\left(0, \begin{bmatrix} \sigma_{z_1}^2 & 0 \\ 0 & \sigma_{z_2}^2 \end{bmatrix}\right)$$

$$\epsilon_{i,j} \overset{iid}{\sim} \text{normal}(0, \sigma_\epsilon^2).$$

The network modeling framework, via the random effects, decomposes the statistical variation in the data to account for (i) the activity level ($a_i$) of each virome i (average amount of sequence space shared across the network for each virome i) and (ii) similarity (clustering) of shared sequence amount among viromes. For ii, $z_i'z_j$ is measure of distance between viromes i and j. Each virome's position ($z_i$) may be visualized in a k-dimensional latent space Z (after a Procrustes' transformation; see below), where virome i and virome j are considered similar if they are close in that space. For ease of visualization a 2D space (k=2; considered a 1D space) (Hoff, *J Am Stat Assoc*, 100(469):286-295 (2005)) was considered.

This modeling approach generalizes stand-alone techniques based on multidimensional scaling [e.g., principle components analysis (PCoA) and nonmetric multidimensional scaling (nMDS)] by embedding an ordination metric $z_i'z_j$ into a single inferential model that additionally accounts for the activity level for each virome in the network and covariates of interest (Chiu & Westveld, *Stat Methodol*, 17(4432):139-160 (2011), Gelman, et al., Bayesian Data Analysis (CRC, Boca Raton, Fla.) (2014), Hoff, et al., *J Am Stat Assoc*, 97(460):1090-1098 (2002), Hoff, *J Am Stat Assoc*, 100(469):286-295 (2005)). Accounting for this dependence structure (expressed by the statistical moments below) allows for appropriate quantification of uncertainty for parameters of interest, including the regression coefficients. The importance of single modeling and inferential framework is highlighted in Gelman, et al., Bayesian Data Analysis (CRC, Boca Raton, Fla.) (2014).

In particular, the error term leads to the following first moment:

$$E(\delta_{i,j})=0,$$

which implies the following first moments for each of the observations:

$$E[\log(\bar{y}_{i,j})]=\log(\bar{n}_{i,j})+\beta'x_{i,j}.$$

The following are the nonzero second and third moments for the errors (as well as the observations). Note that even though the data are dyadic, the third moment is not equal to zero $$E(\delta_{i,j}^2)=E(\delta_{i,j}\delta_{j,i})=E(\delta_{j,i}^2)=2\sigma_a^2+\sigma_\epsilon^2+\sigma_{z_1}^4+\sigma_{z_2}^4$$

$$E(\delta_{i,j}\delta_{i,k})=E(\delta_{i,j}\delta_{k,j})=E(\delta_{i,j}\delta_{k,i})=\sigma_a^2$$

$$E(\delta_{i,j}\delta_{j,k}\delta_{k,i})=\sigma_{z_1}^6+\sigma_{z_2}^6.$$

To estimate the parameters in the model, a Bayesian inferential approach was considered using the R statistical software (Hoff, *J Am Stat Assoc,* 102(478):674-685 (2007)) and gbme.R obtained from Chiu & Westveld, *Stat Methodol,* 17(4432):139-160 (2011) (stat.washington.edu/hoff/Code/hoff_2005_jasa). For the analyses, empirical Bayes priors were considered (the default for the gbme.R). To examine the joint posterior distribution of the parameters, a Markov chain of 1,000,000 scans was constructed. The first 500,000 scans were removed for burn-in, and the chain was thinned by every 100th scan, leaving 5,000 samples.

Procrustes transformation.

Although the inner products ($z_i'z_j$) are identifiable, individually the random effects ($z_i$) corresponding to the latent space are unidentifiable without constraints (Chiu & Westveld, Stat Methodol, 17(4432):139-160 (2011), Gelman, et al., Bayesian Data Analysis (CRC, Boca Raton, Fla.) (2014), Kass & Raftery, *J Am Stat Assoc,* 90(430):773-795 (1995)). Specifically, the inner products are invariant to rotation and reflection of the latent space Z. To circumvent this unidentifiability for visualization, for each sth Markov chain Monte Carlo (MCMC) scan, a Procrustes transformation is applied to rotate the space to a common orientation.

Goodness-of-Fit.

The Akaike and Bayesian information criteria (AIC and BIC) was reported to compare the network mixed model (based on Eqs. S1 and S2) to a simpler standard regression model $$\log(\bar{y}_{i,j}) = \log(\bar{n}_{i,j}) + \beta' x_{ij} + \epsilon_{ij} \quad [S3]$$

$$\epsilon_{i,j} \overset{iid}{\sim} \text{normal}(0, \sigma_\epsilon^2).$$

Specifically, the following criteria was considered:

AIC=−2 log $p(y|\hat{\theta}_{Bayes})$+2k

BIC=−2 log $p(y|\hat{\theta}_{Bayes})$+k log(N), where k is the number of parameters, and N is the number of data points. The log likelihoods were evaluated at the means of the posterior distributions [θBayes=E(θ|y)] (McCullagh & Nelder, Generalized Linear Models (CRC, Boca Raton, Fla.) (1989), Muller, et al., *Stat Sci,* 28(2):135-167 (2013)); please see R Core Team, R: A Language and Environment for Statistical Computing (R Foundation for Statistical Computing, Vienna) (2013) for an overview of model selection for mixed models. In considering the effective number of parameters for the random effects portion of the network model, additional number of parameters compared with the standard regression model, used were both an optimistic (o) lower bound, consisting of three additional parameters ($\sigma_a^2$, $\sigma_{z1}^2$, $\sigma_{z2}^2$) and a pessimistic (p) upper bound where all of the random effects were treated as fixed ($s_i$, $z_i$, $\forall_i$={1, . . . , A=number of nodes}; leading to 3×A additional parameters).

Based on the AIC values, for both the optimistic and pessimistic effective number of parameters, the network model is preferred to the standard regression model. The same holds true for the BIC values, except for one case (the pessimistic effective number of parameters for LineP open ocean data). Overall these results suggest that the network structure is an important consideration when modeling relational metagenomics data.

Results

Microorganisms drive global biogeochemical cycles (Falkowski, et al., *Science,* 320(5879):1034-1039 (2008), with abundances and taxonomic composition tuned to spatio-temporally varying environmental conditions (Caporaso, et al., *ISME J,* 6(6):1089-1093 (2012), Chow, et al., *Environ Microbiol,* 14(8):2171-2183 (2012), Fortunato, et al., *ISME J,* 6(3):554-563 (2012), Zaikova, et al., Environ Microbiol, 12(1):172-191 (2010)). Viruses then modulate these biogeochemical processes through mortality, horizontal gene transfer, and metabolic reprogramming (Breitbart, *Annu Rev Mar Sci,* 4:425-448 (2012)). However, our understanding of how viral communities change in response to biological, physical, and chemical factors and host availability has been limited by technical challenges.

Most viruses in the ocean lack both cultivated representatives [85% of 1,100 sequenced phage genomes derive from only 3 of 45 bacterial phyla (Holmfeldt, et al., *Proc Natl Acad Sci,* USA 110(31):12798-12803 (2013))] and a universally conserved marker gene (Edwards & Rohwer, *Nat Rev Microbiol,* 3(6):504-510 (2005)); thus, metagenomics is commonly applied to characterize the ecology and evolution of viral assemblages. Problematically, however, the ability to investigate these assemblages via metagenomics remains limited by the lack of known viruses and viral proteins in biological sequence databases. The first viral metagenome (virome) used thousands of Sanger reads and found that 65% of sequences were unknown [i.e., no database match for reads >600 bp (Breitbart, et al., *Proc Natl Acad Sci, USA,* 99(22):14250-14255 (2002))]. Adoption of next-generation sequencing (NGS) technologies then generated hundreds of thousands of reads (averaging 102 bp in length) per virome and returned ~90% sequence novelty (Angly, et al., *PLoS Biol,* 4(11):e368 (2006)). This unknown problem has not been significantly improved on in subsequent oceanic virome studies regardless of sequencing platform (Hurwitz & Sullivan, *PLoS ONE,* 8(2):e57355 (2013)). This novelty limits taxonomic and functional inferences about viral assemblages and makes comparative analyses that only use the known portion of these datasets minimally informative at best and completely misleading at worst. Additionally, the standard practice of comparing new datasets against large genomic databases is compute intensive and increasingly unfeasible given escalating scales in datasets and databases.

To circumvent similar issues, Yooseph et al. (Yooseph, et al., *PLoS Biol,* 5(3):e16 (2007)) clustered environmental reads with known proteins from available databases to define sequence similarity-based protein clusters (PCs) to analyze the first global ocean microbial metagenomic datasets. This PC approach helps to both organize the vastly unknown sequence space in metagenomes and identify abundant proteins in environmental datasets even where taxonomy and function are unknown. Application of this approach to viromes has also been fruitful and has led to (i) a dataset of 456K protein clusters (Hurwitz & Sullivan, *PLoS ONE,* 8(2):e57355 (2013)), (ii) comparative estimates of viral community diversity across sites (Hurwitz & Sullivan, *PLoS ONE,* 8(2):e57355 (2013), Hurwitz, et al., *Environ Microbiol,* 15(5):1428-1440 (2013)), and (iii) an estimate that the global virome is three orders of magnitude less diverse than previously thought (Ignacio-Espinoza, et al., *Curr Opin Virol,* 3(5):566-571 (2013)). Although a valuable approach for metagenomic data, particularly for viromes where functional and taxonomic information is especially limiting, there are drawbacks to the PC approach including (i) only mapping ~75% of the data (Hurwitz & Sullivan, *PLoS ONE,* 8(2):e57355 (2013)) and (ii) a reliance on metagenomic assembly algorithms not yet optimized for handling sequence variation derived from sequencing artifact and real population heterogeneity (Degnan & Ochman, *ISME J*, 6(1):183-194 (2012)).

Recently, k-mer-based approaches were introduced to facilitate genome annotation (Edwards, et al., *Bioinformatics*, 28(24):3316-3317 (2012)) and for whole genome comparison to identify relationships among organisms without assembly and synteny analysis (Song, et al., *J Comput Biol*, 20(2):64-79 (2013)). For larger-scale metagenomic datasets, this approach offers a computationally scalable option for direct comparisons. Specifically, this shared k-mer strategy enables a similarity metric and the ability to identify clusters of metagenomes to infer how microbial communities are affected by environmental factors (Jiang, et al., *BMC Genomics*, 13:730 (2012)). These are significant advances, but they suffer from the lack of a unified statistical framework for evaluating genetic predictors of community structure based on multiple ecological variables that can be dependent on one another.

Here, a strategy is introduced to comparatively evaluate complete metagenomes by combining a shared k-mer approach with social network analysis to place all data into a unified context. Expanding on prior k-mer-based metagenomic methods (Song, et al., *J Comput Biol*, 20(2):64-79 (2013), Jiang, et al., *BMC Genomics*, 13:730 (2012)), a model was used to determine the statistical significance of ecological variables in forming the network while also accounting for dependency among these variables. The resulting network allows for data-driven hypothesis testing and generation through the evaluation of k-mer-based virome proximity in network space and statistical evaluation of ecological variables that drive these relationships. Application of this approach to 32 Pacific Ocean viromes (POVs) reveals a high-level overview of shared sequence space between these viromes, investigates the environmental characteristics that drive variability in viral community structure, and identifies testable hypotheses regarding viral community dynamics Finally, although demonstrated on viromes, this strategy can be efficiently implemented on many large-scale sequence datasets with broad uses from environmental to clinical applications.

Similar to previous metagenomic studies of ocean viruses (Breitbart, et al., *Proc Natl Acad Sci USA*, 99(22):14250-14255 (2002), Angly, et al., *PLoS Biol*, 4(11):e368 (2006), Dinsdale, et al., *Nature*, 452(7187):629-632 (2008), Williamson, et al., *PLoS ONE*, 3(1):e1456 (2008), Bench, et al., *Appl Environ Microbiol*, 73(23):7629-7641 (2007)), the 6,000,000 read POV dataset was dominated by the unknown (<6% of reads matched known viruses) (22). To more holistically compare viral metagenomes in a computationally scalable way (57× faster than BLAST and comparable to heuristic clustering algorithms), a strategy was employed using read-level k-mer similarity analyses between viromes as input to a social network analysis (SNA) to model relationships between viromes and metadata using statistical regression methodologies (Hoff, *J Am Stat Assoc*, 100(469): 286-295 (2005), Chiu & Westveld, *Proc Natl Acad Sci USA*, 108(38):15881-15886 (2011), Hurwitz, et al., *Genome Biol*, 14(11):R123 (2013)). These analyses resulted in (i) a unified comparative network of viromes based on sequence composition (FIGS. 7A-7D) and (ii) a statistical measure of the effect of covariates (i.e., season, proximity to shore, and depth) on the network structure using Eq. 1 (Table 1). This technique was applied to the complete dataset and two subsampled datasets to examine broad-scale, temporal, and spatial patterns as follows: (i) all 32 Pacific Ocean samples (FIGS. 7A and 7B), (ii) open ocean, station P26 LineP samples that vary by season and depth (FIG. 7C), and (iii) spring LineP transect samples that vary by proximity to shore and depth (FIG. 7D).

TABLE 1

Bayesian inference numerical summaries for social networks with selected covariates

| Network dataset/Covariate | Parameter | Posterior median | Lower limit credible interval (2.5%) | Upper limit credible interval (97.5%) |
|---|---|---|---|---|
| Full dataset [32 samples (nodes)] | | | | |
| $\log(\bar{\eta}_{i,j})\log(\bar{\eta}_{i,j})$ | γ | 0.63 | 0.42 | 0.88 |
| Geographic region | $\beta_1$ | 0.14 | 0.06 | 0.21 |
| Depth | $\beta_2$ | 0.12 | 0.06 | 0.19 |
| Season | $\beta_3$ | 0.03 | −0.02 | 0.08 |
| Proximity to shore | $\beta_4$ | 0.12 | 0.08 | 0.16 |
| Oxygen | $\beta_5$ | −0.00 | −0.21 | 0.08 |
| LineP open ocean [11 samples (nodes)] | | | | |
| $\log(\bar{\eta}_{i,j})\log(\bar{\eta}_{i,j})$ | γ | 0.828 | 0.206 | 1.298 |
| Depth | $\beta_1$ | 0.224 | 0.11 | 0.343 |
| Season | $\beta_2$ | 0.124 | 0.032 | 0.257 |
| Oxygen | $\beta_3$ | −0.336 | −0.589 | −0.084 |
| LineP spring transect [11 sample (nodes)] | | | | |
| $\log(\bar{\eta}_{i,j})\log(\bar{\eta}_{i,j})$ | γ | 6.737 | 5.555 | 7.874 |
| Depth | $\beta_1$ | 0.117 | −0.053 | 0.287 |
| Proximity to shore | $\beta_2$ | 0.047 | −0.063 | 0.147 |
| Oxygen | $\beta_3$ | 0.867 | 0.253 | 1.205 |

Statistically significant covariates for each network are shown m bold. Covariates are considered significant if the upper and lower credible intervals (Baysian confidence intervals) do not overlap with zero. The covariate $\log(\bar{\eta}_{i,j})\log(\bar{\eta}_{i,j})$ is an offset (although the coefficient was not restricted to be equal to 1), which accounts for the fact that more shared read space may occur between two viromes if the either of the viromes is larger.

Broad-Scale Patterns Across 32 Pacific Ocean Viral Communities.

Visually, eight regions emerged from the full 32 POV network that broadly differed by photic zone (three photic vs. five aphotic; FIG. 7A). In the aphotic portion of the network, the first region contained three viromes from summer at LineP open ocean station P26 and the second region contained three spring LineP samples from deep samples of the transect. The third region in the aphotic region of the network contained viromes from all three biomes with deep samples and across seasons, whereas the fourth and fifth regions contained outlier LineP spring viromes sampled from the base of the oxygen minimum zone.

A sixth region, in the photic portion of the network, contained all four of the spring/summer surface ocean LineP samples regardless of whether they were coastal, intermediate, or open ocean stations, as well as one Monterey Bay (MBARI) virome sampled in fall from the deep chlorophyll maximum (DCM; 42 m) at an intermediate ocean transect site. The seventh region contained surface water viromes including four near-replicate viromes [a single viral-concentrate that was differentially concentrated or purified (Hurwitz, et al., *Environ Microbiol*, 15(5):1428-1440 (2013))], sampled in the spring from Scripps Pier, one MBARI fall coastal virome, and one LineP winter open ocean virome. Finally, an eighth region contained five viromes including three from the MBARI photic zone at intermediate and open ocean stations and two shallow samples from the Great Barrier Reef.

To complement these overall qualitative patterns (based on quantitative underpinnings), a unified network regression model was also used to evaluate ecological drivers of the observed network structure. Here, biogeographic region, depth, and proximity to shore were significant predictors of the overall POV network, but season was not (Table 1). Overall, only 3% of reads (n=196,924) were universal to all samples within the POV network, whereas 23% and 10% of reads were exclusive to photic or aphotic parts of the network, respectively (FIG. 7B). The four near-replicate viromes from Scripps Pier contained the most activity (shared reads) in the network, whereas the shallow Great Barrier Reef viromes and one MBARI virome had the least.

Finer-Scale Patterns Across Subnetworks.

Given the complexity of the overall POV network, smaller refined subnetworks were examined to differentiate spatiotemporal features. First, analyses were focused on the most temporally well-resolved subsets of samples that included 11 viromes from the LineP open ocean P26 station. Visually, again upper ocean, photic zone viromes were clearly separated from deep water, aphotic zone viromes, with seasonality leading to structure within these zones (FIG. 7C). Statistical regressions suggested that ecological drivers included depth, season, and oxygen concentration (Table 1).

A second subset of the data from LineP allowed focus on spatial variability from the coastal to open ocean samples collected on a springtime research cruise (FIG. 7D). Visually, again the photic and aphotic zone viromes were separated in shared k-mer space, but this time no strong patterns were observed with depth within these larger zones or with proximity to shore. Statistical analyses supported these qualitative observations, as only oxygen represented a structuring factor (Table 1).

LineP: A Case Study in Niche Specialization by Season.

The power of the above analyses is the ability to visually represent viromes and define significant metadata factors to drive further investigation into underlying patterns. Given that reads have associated abundances (via the k-mer mode; FIG. 8), reads that are exclusive to specific viromes or parts of the network can be mined out of the underlying data. This is demonstrated by examining reads that are distinct by season (summer vs. winter) and photic zone (photic vs. aphotic) at open ocean station P26 at LineP in the Pacific Ocean based on FIG. 7C and Table 1. The exclusive read data demonstrate metabolic differences in parts of the network that likely derive from viral-encoded auxiliary metabolic genes as follows, given the purity of these viromes (Hurwitz & Sullivan, *PLoS ONE*, 8(2):e57355 (2013), Hurwitz, et al., *Environ Microbiol*, 15(5):1428-1440 (2013), Sharon, et al., *ISME J*, 5(7):1178-1190 (2011)).

The largest proportion of exclusive reads in all viromes, irrespective of photic zone or season, encodes genes related to nucleotide metabolism. Given that viruses require nucleotides for replication, this result is not unexpected. When broadly comparing the photic zone and aphotic zone, aphotic viromes contain more overall metabolic functional capacity. In particular, genes related to the tricarboxylic acid (TCA) cycle, mannose and fructose metabolism, and electron transport chain (ETC) are more highly represented in aphotic viromes and are likely involved in energy production (Sharon, et al., *ISME J*, 5(7):1178-1190 (2011)). These genes may be less represented in photic samples, given the capacity for viruses to encode and express photosynthetic genes (Breitbart, *Annu Rev Mar Sci*, 4:425-448 (2012)) that allow them to derive energy for phage replication. Fatty acid metabolism may also be a source of energy production in phage in all seasons and photic zones, but most highly represented in summer aphotic viromes perhaps due to increased phage production in the summer and less energy derived from other sources. Interestingly, aphotic viromes and winter photic viromes contain genes related to cysteine and methionine metabolism, whose role is currently unknown but may be related to scavenging iron from Fe—S clusters in iron limited regions given that cysteine is important for Fe—S cluster biogenesis and degradation (Zhang, et al., *Food Microbiol*, 31(2):285-292 (2012)). Last, pyrimidine, purine, and glutathione metabolism may be important in winter aphotic viromes. Given that glutathione improves cold resistance in bacteria (Breitbart & Rohwer, *Trends Microbiol*, 13(6):278-284 (2005)), viruses may help to provide protection to their infected hosts in the winter. These data suggest that viruses coevolve with their hosts and bolster host metabolism to improve host vitality for phage production given environmental selective pressures on the host.

Discussion

Microbes are now well recognized as critical players in ecosystems ranging from oceans and soils to humans and bioreactors. Their viruses are often as important, but methodological challenges have made it difficult to investigate even relatively fundamental questions such as how viral communities change over space and time. All currently used methods (e.g., morphology, viral genome fingerprinting, single-gene analyses, database-dependent annotation, and PC-based metagenomics) have issues that prevent extrapolating inferences to whole viral communities. The approach presented here that combines shared k-mer and social network analysis uses all of the reads, does not require assembly or database-dependent annotation, and includes a statistical framework (i.e., regression modeling) to evaluate ecological drivers of the resulting network structure. Application to 32 Pacific Ocean viromes allowed us to test hypotheses about how viral communities change over space and time, as well as generate new hypotheses where expectations were not met.

Broad-Scale Inferences about Pacific Ocean Viral Communities.

Comparisons made across the entire POV dataset revealed that seasonality and oxygen were relatively unimportant in structuring viral communities, whereas geography, depth, and proximity to shore were significant. These first findings, that seasonality and oxygen do not structure POV communities, are likely a result of the overall dataset containing samples with many differing ecological features: e.g., half the dataset is associated with an oxygen minimum zone (LineP) and the rest have relatively invariant oxygen conditions. Thus, other features that strongly vary within the dataset overwhelm the more specific effects of season and oxygen (but see discussion of subnetworks below).

That geography is a strong driver of viral community structure is striking as ocean viruses have been posited to have extensive dispersion capability [inferred from global distribution of identical genetic marker sequences (Brum, et al., *ISME J*, 7(9):1738-1751 (2013))] and a recent morphological survey of ocean viral communities found that geographic distance was not significant in explaining their variability across six oceans and seas (Duhaime & Sullivan, *Virology*, 434(2):181-186 (2012)). However, genome-wide variation likely far exceeds that of highly conserved marker genes and morphology-based metrics. A previous metagenomic study also suggested that four spatially diverse ocean viral communities were quite different (Angly, et al., *PLoS Biol*, 4(11):e368 (2006)), but the viromes were prepared in a nonquantitative manner (Ladau, et al., *ISME J*, 7(9):1669-1677 (2013)), and only the known portion of these viromes (~2% of the total reads with annotation to known phage) were analyzed to make this inference. The observation of geographic variability in total viral metagenomes is consistent with variability of their dominant hosts, bacteria, which have geographic variability at the community level (Jiang, et al., *BMC Genomics*, 13:730 (2012), Brown, et al., *Mol Syst Biol*, 8:595 (2012)), as well as within abundant phyla, including either large-scale genomic changes (e.g., in Pelagibacter) (Coleman & Chisholm, *Trends Microbiol*, 15(9):398-407 (2007)) or small-scale genomic changes more strongly localized to genomic islands (e.g., in cyanobacteria) (Weinbauer, *FEMS Microbiol Rev*, 28(2):127-181 (2004)).

Beyond geography, both depth and proximity to shore represent some of the strongest gradients available in the oceans, so it is not surprising they might also structure viral community composition across this larger sample set. Total viral particle counts broadly mirror those of prokaryotes across depth profiles in the oceans (DeLong, et al., *Science*, 311(5760):496-503 (2006)), which suggests that as microbial population abundances and structure change with depth, so too would their viruses. For example, microbial metagenomes from an open ocean depth profile show cyanophage abundance broadly mirrors that of their hosts (Jiang, et al., *Microb Ecol*, 45(4):399-410 (2003)). As well, depth-related variability in extracellular marine viral communities has been documented using viral genome fingerprinting (Steward, et al., *Limnol Oceanogr* 45(8):1697-1706 (2000), Freeland, *Prog Oceanogr*, 75(2):120-125 (2007)), and the findings support this, showing that depth is a clear driver of viral community structure. The latter driving factor, proximity to shore, is discussed with the subnetwork findings below.

Finer-Scale Evaluation of Ecological Factors that Structure Viral Communities.

The decades of study along the LineP oceanographic transect (Whitney, et al., *Prog Oceanogr* 75(2):179-190 (2007)) present an ideal backdrop for investigating temporal and spatial variability in viral communities. To focus on temporal variability, a subnetwork of 11 viromes from February (winter), June (spring), and August (summer) at a single LineP station (open ocean station P26) was examined. This analysis revealed that depth, season, and oxygen were significant drivers of viral community structure in this subset of the data. In addition to the discussion of depth above, it is noteworthy that the LineP transect region is strongly stratified to the point of establishing one of the largest ocean interior oxygen minimum zones (Parsons, et al., *ISME J*, 6(2):273-284 (2012)), so it is not surprising that viral community structure would significantly vary with depth and oxygen. That seasonality was also a driver is consistent with studies demonstrating annual cyclical changes in marine bacterial community structure (Chow, et al., *Environ Microbiol*, 14(8):2171-2183 (2012), Gilbert, et al., *ISME J*, 6(2):298-308 (2012), Wright, et al., *Nat Rev Microbiol*, 10(6):381-394 (2012)). Although the single-year virome dataset does not permit inferences about year-to-year variation, similar annual repeatability has been observed in total viral abundance at the Bermuda Atlantic Time Series station (Gilbert, et al., *ISME J*, 6(2):298-308 (2012)), suggesting that annual repeatability of microbial hosts may lead to the same for their viral predators.

Additionally, the LineP transect is ideal for evaluating spatial changes in viral community structure along coastal to open ocean gradients. The strong vertical oxygen gradients along this transect (Brum & Steward, *Microb Ecol*, 60(3):636-643 (2010)) structured the viral community in the temporally focused subnetwork analysis above and also do so here in the spatial subnetwork analysis for a single season. Mechanistically, these strong gradients in oxygen are likely structuring LineP microbial populations as observed for total bacterial community composition (Brum & Steward, *Microb Ecol*, 60(3):636-643 (2010)) and dominant bacterial phyla [e.g., SUP05 and Marine Group A (MGA) (Brum & Steward, *Microb Ecol*, 60(3):636-643 (2010))], which in turn structure their viral communities. These results are supported by studies of viral communities along strong oxygen gradients in stratified lakes using morphology or viral genome fingerprinting (Steward, et al., *Limnol Oceanogr*, 45(8):1697-1706 (2000), Cassman, et al., *Environ Microbiol*, 14(11):3043-3065 (2012)), as well as a metagenomic investigation of viruses in a marine oxygen minimum zone off of Chile (Whitney, et al., *Deep Sea Res Part II Top Stud Oceanogr*, 52(5):681-706 (2005)).

Notable outliers in this dataset include viromes from the base of the deep ocean oxycline (LineP spring 2,000-m viromes from the intermediate and open ocean). Distinct viral communities have been observed within oxyclines of marine and saline lake environments (Cassman, et al., *Environ Microbiol*, 14(11):3043-3065 (2012), Whitney, et al., *Deep Sea Res Part II Top Stud Oceanogr*, 52(5):681-706 (2005)), and thus these samples may represent viruses infecting bacteria adapted to dysoxic conditions (Brum & Steward, *Microb Ecol*, 60(3):636-643 (2010)). Alternatively, these deep oxycline viral communities could include surface water viruses that were entrapped on sinking particles and released at depth as a result of degradation, explaining their greater similarity to photic zone samples.

Additionally, although proximity to shore was a significant driver of viral community variability in the network with all samples, it was not significant when focusing solely on the LineP transect despite gradients in nutrients and productivity that occur along this transect (Allers, et al., *ISME J*, 7(2):256-268 (2013)). A lack of spatial variability in abundance of a specific bacterial phyla (MGA) along this transect has been observed (Dinsdale, et al., *Front Genet*, 4:41 (2013)), supporting these findings. Thus, the change in significance of proximity to shore as a structuring variable may be explained in the same fashion as for oxygen concentration. Specifically, the inclusion of coastal samples from MBARI, Scripps Pier, and the Great Barrier Reef may have been the primary drivers of this relationship in the full sample network, and their exclusion in the LineP transect network resulted in oxygen being the overwhelmingly dominant structuring variable, as was also noted for MGA distribution along this transect (Dinsdale, et al., *Front Genet*, 4:41 (2013)).

Last, it is noted that activity between viromes (shared reads) varies with sequencing effort. Four deeply sequenced near-replicate viromes from Scripps Pier showed the highest activity with other viromes likely due to greater representation of reads derived from the rare virosphere. Because the network is normalized for sequencing effort, this does not affect network structure, but is important when considering activity between viromes.

Analytical Advances.

The approach outlined here provides a significant advance over alternative ecological methods for dimensionality reduction such as principle components analysis (PCoA) and nonmetric multidimensional scaling (nMDS; for details, see SI Methods). Broadly, the contrast lies in the fact that PCoA and nMDS are generally descriptive approaches (Huttenhower, (2014) MaAsLin: Multivariate analysis by linear models, http://huttenhower.sph.harvard.edu/maaslin. Accessed Dec. 30, 2013), whereas the network approach outlined here provides a full inferential framework. Specifically, relational data methods are used to create a dependence structure in ordination space that includes random effects and as a result allows for the proper inference for regression coefficients (i.e., metadata). Or, in simple terms, the distances between viromes based on shared reads can be visually represented, while at the same time accounting for biological factors in a single statistical model. The importance of single modeling and inferential framework is highlighted in Chiu and Westveld (Hurwitz, et al., *Genome Biol*, 14(11):R123 (2013)).

This approach is also inherently different from other statistical frameworks [e.g., MaAsLin (Hurwitz, (2014), http://code.google.com/p/tmpl. Accessed Dec. 30, 2013)] that identify associations between metadata and the abundance of operational taxonomic units (OTUs) or functions in metagenomic samples. Specifically, MaAsLin outputs a list of OTUs or functions that are significant given a metadata type. Given that the results are granular (by OTU or function) and only account for only one metadata type at a time, they cannot be combined. In contrast, this analytical framework (i) uses a model that enables simultaneous examination of shared sequence space between viromes in conjunction with multiple metadata types and (ii) requires no prior organizational bins (e.g., OTUs for MaAsLin), which is critical for viruses that lack a universal barcode gene for such taxonomic assignments. Both advances are fundamental for surveying complex viral communities to look for ecological drivers of community structure but also help broaden the toolkit available for other comparative metagenomic datasets (e.g., bacterial).

This approach may also prove to be important in other microbial analyses wherein taxonomic identification is less of a concern given rRNA sequence datasets. Specifically, entire metagenomes were used rather than a single gene (like 16S in bacteria) to assess the composition of microbial communities. The use of complete metagenomes is particularly important in cases where metagenomes may contain closely related species, indistinguishable on the level of the 16S gene alone, that have functional differences that make them distinct.

Further, because reads that represent significant patterns in the network can be mined out (see results LineP seasonal niche differentiation), this approach drives functional comparative metagenomic analyses. This approach is also important pragmatically in terms of runtime because fewer reads require extensive functional annotation. Moreover, the remaining unknown fraction of reads exclusive to a certain part of the network provides a starting point for future empirical analyses to understand the function of novel viral species. This approach is broadly applicable to metagenomes comprised of any microbe from viruses, to bacteria or fungi, and extends current approaches through the use of whole metagenomes and a comprehensive statistical framework.

CONCLUSIONS

Although marine microbes and their viruses are fundamental to Earth system function, the culture-independent metagenomic techniques used to study them present "big data" analytical challenges. The combination of shared k-mer and social network analysis presented here provides a powerful way to visualize and explore relationships between metagenomic samples and populations and statically evaluate the underlying factors that drive this variability. These methods are computationally tractable and widely applicable across sequence datasets and have the capacity to affect how data are stored, visualized, and analyzed, making use of big data analytics and the large-scale context that is now becoming available in metagenomic data repositories. These types of analyses and scales of data are needed to predictively model Earth's most abundant biological entities, viruses, and their predominant hosts, microorganisms.

It is contemplated that this method can be applied to bacterial communities in wounds, to cluster patient samples in a network and determine which factors (e.g., antibiotics, negative pressure therapy, and/or behavior) play a significant role in clinical outcome. This allows for a direct analysis of the interplay between bacteria in a wound, a patient's response to infection, treatment, and the healing process, towards better clinical care and reduced cost. This approach can also be used to identifying biomarkers for development of new rapid tests that use the biomarkers as surrogates for the presence of particular bacterial species or genes with clinical significance. Using the network as a guide, reads that are unique to certain parts of the network can be identified and used as "gene signatures". Gene signatures can be annotated to examine taxonomy and function in parts of the network that differentiate samples. Or, in the case of unknown sequences that differentiate clusters of "healers" and "non-healers" empirical follow up analyses can fuel exploratory biology in infections with fastidious or unknown organisms.

These gene signatures can categorize wounds irrespective of whether they come from well-documented clinical microbes or novel bacteria, fungi, viruses, and/or parasites.

Wounds, specifically, diabetic foot ulcers, provide a perfect clinical entry point for analysis of infections, such as bacterial, fungal, viral and or parasitic infections, given that they are easily monitored and biopsied in normal patient care. In one example, wound biopsies will be collected from patient cohorts with diabetic foot ulcers (DFU), DNA extracted and sequenced and the data correlated with health "factors" gleaned from electronic health records data using the network approach described above to determine clinical factors associated with wound samples that cluster with "healers" versus "non-healers". Given varied treatment, bacterial community composition will be correlated with patient outcome and response to a variety of treatments. Further, patients will be followed through their typical treatment regimens and data will be collected for multiple time points for a single patient as the DFU heals. These data will provide fundamental information about the healing process and provide a survey of bacterial communities that comprise the healing spectrum.

Example 2

Figure 10:
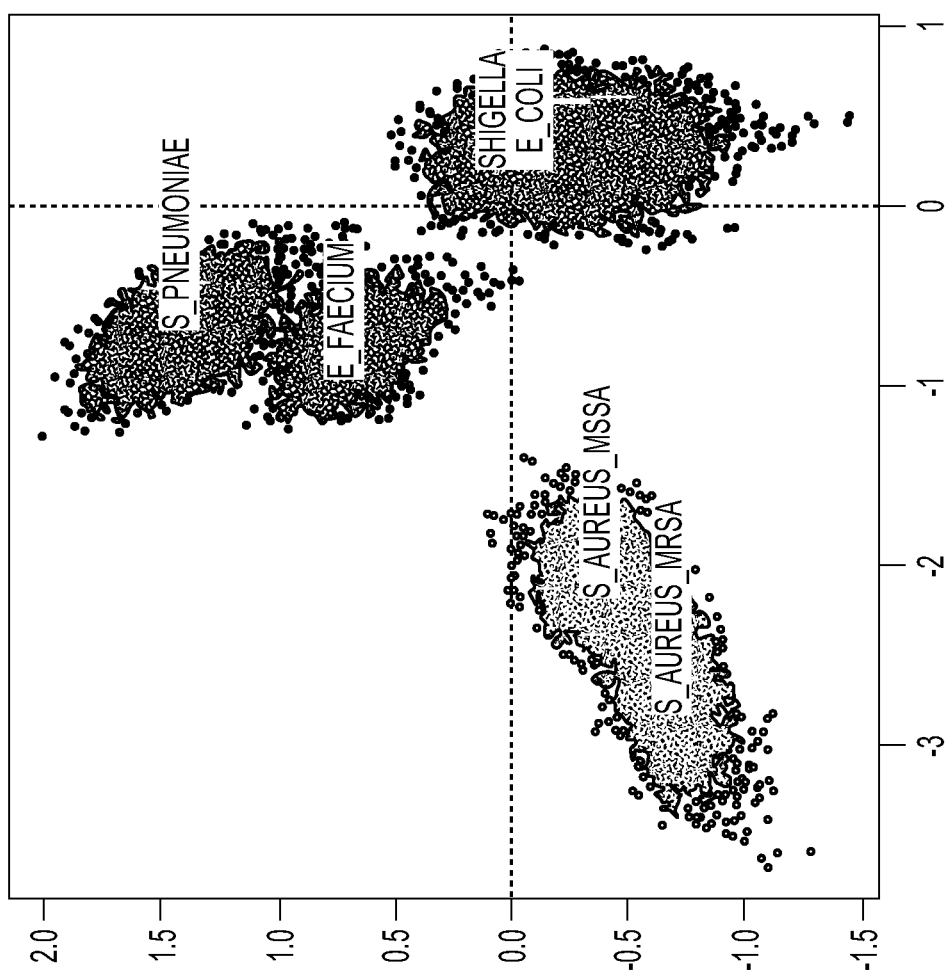
FIG. 10 is an image created by using ion torrent data in which strain isolates were sequenced using whole genome shotgun sequencing and the disclosed method was applied to the resulting data.

This example illustrates the disclosed method as applied to strain isolates. FIG. 10 illustrates that the pure strains form different clusters based on their sequence that will allow one to place unknown clinical isolates in a "clinical bacterial sequence map". For example, one can also see differences in closely related strains (e.g., *S. aureus* with methicillin sensitive (MSSA) versus with methicillin resistant *Staphylococcus aureus* (MRSA)). In this embodiment, FIG. 10 was produced by sequencing gDNA from strain isolates using ion torrent sequencing technology (here after "strain isolate whole genome shotgun (WGS) sequencing"), performing quality control on the reads from the strain isolate WGS, creating suffix arrays of k-mers from each strain isolate WGS, performing a pairwise analysis of each read from the strain isolate WGS versus suffix arrays, creating a matrix of the number of "shared reads" between pairs of strain isolate WGS samples (wherein reads were considered shared if their mode k-mer abundance value was >1), and performing a Bayesian network analysis per the disclosed method. Data in WGS data from strain isolates represented in random fragments of each genome, with approximately –200K high quality reads per strain isolate WGS, with read lengths between 75-250 base pairs.

In view of the many possible embodiments to which the principles of our invention may be applied, we claim as our invention all such embodiments as may come within the scope and spirit of the following claims and equivalents thereto.

As will be appreciated by those ordinary skilled in the art, the foregoing example, demonstrations, and method steps may be implemented by suitable code on a processor base system, such as general purpose or special purpose computer. It should also be noted that different implementations of the present technique may perform some or all the steps described herein in different orders or substantially concurrently, that is, in parallel. Furthermore, the functions may be implemented in a variety of programming languages. Such code, as will be appreciated by those of ordinary skilled in the art, may be stored or adapted for storage in one or more tangible machine readable media, such as on memory chips, local or remote hard disks, optical disks or other media, which may be accessed by a processor based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in a computer memory.

While the following description is presented to enable a person of ordinary skill in the art to make and use the invention, it is provided in the context of the requirement for a obtaining a patent. The present description is the best presently-contemplated method for carrying out the present invention. Various modifications to the preferred embodiment will be readily apparent to those skilled in the art and the generic principles of the present invention may be applied to other embodiments, and some features of the present invention may be used without the corresponding use of other features. Accordingly, the present invention is not intended to be limited to the embodiment shown but is to be accorded the widest scope consistent with the principles and features described herein.

Many modifications of the present invention will be apparent to those skilled in the arts to which the present invention applies. Further, it may be desirable to use some of the features of the present invention without the corresponding use of other features.

Accordingly, the foregoing description of the present invention should be considered as merely illustrative of the principles of the present invention and not in limitation thereof.

We claim:

1. A method comprising:
   (i) obtaining a plurality of sequencing reads of DNA from a biological sample of a subject suspected of containing an infection;
   (ii) computer-implemented steps of:
      (a1) deconstructing biological sample k-mers from a biological sample sequencing read;
      (b1) comparing the biological sample k-mers to a suffix array of k-mers deconstructed from sequencing reads from a clinical sample for which the clinical outcome is known;
      (c1) counting how many times each biological sample k-mer appears in the clinical sample suffix array to determine the mode k-mer value for the biological sample sequencing read;
      (d1) optionally repeating steps (b1)-(c1) with one or more additional biological sample sequencing reads;
      (e1) optionally repeating steps (b1)-(d1) with one or more additional clinical samples;
      (f1) establishing a read abundance value for the biological sample read(s) in the clinical sample by using the mode k-mer value(s) obtained according to steps (c1)-(d1) greater than zero to calculate the proportion of reads shared between the biological sample and the clinical sample; and
      (g1) repeating step (f1) for each additional clinical sample of step (e1);
      (h1) using a network modeling framework to compute the average amount of sequence space shared across the network for each sample, and similarity of shared sequence amount among the samples,
      deriving one or more relational covariates from clinical parameters associated with the patients from which the biological sample and clinical sample(s) were obtained, and
      estimating the clinical parameters in the model using value decomposition and regression;
      optionally wherein the relational covariate(s) comprise one or more of risk factors, weight, age, sex, blood glucose, clinical outcome, and response to treatment(s); and
      optionally visualizing the relative positions of each sample in the network;
   (iii) prognosing the infection comprising using the network as a representation of the similarity between the biological sample and the clinical sample or samples, the correlation of which is used to predict the outcome of the suspected infection in the biological sample; and
   (iv) providing a treatment to the subject for the infection, wherein the treatment comprises administration of an antimicrobial agent, pressure bandage, negative pressure therapy, or a combination thereof, and is predicted to have a positive impact on the infection based upon the prognosis thereof.

2. The method of claim 1, wherein the biological sample is from a wound of a subject.

3. The method of claim 1, further comprising creating a table showing the mode k-mer values, creating a read abundance matrix comprising the read abundance values, or a combination thereof.

4. The method of claim 1, wherein the network modeling framework of (h1) comprises a Bayesian inferential approach comprising measuring the distance and similarity between samples; and
   wherein (h1) comprises visualizing each sample's position in a k-dimensional latent space Z.

5. The method of claim 4, further comprising identifying biomarkers specific for one or more microbes in the biological sample.

6. The method of claim 4, wherein the joint posterior distribution of the parameters of (h1) are examined via a Markov chain.

7. A system for prognosing infection in a sample, comprising: one or more processors; and one or more non-transitory computer readable storage media storing computer readable instructions that when executed by the one or more processors cause the processors to perform the method of claim 1.

8. The method of claim 1, wherein the infection is polymicrobial.

9. The method of claim 1, step (ii) further comprising
(a2) preparing a suffix array of the biological sample k-mers;
(b2) comparing clinical sample k-mers deconstructed from a sequencing read of DNA from the clinical sample to the suffix array of biological sample k-mers;
(c2) counting how many times each clinical sample k-mer appears in the biological sample suffix array to determine the mode k-mer value for the clinical sample sequence read;
(d2) optionally repeating steps (b2)-(c2) with one or more additional clinical sample sequencing reads;
(e2) optionally repeating steps (b2)-(d2) with one or more additional clinical samples;
(f2) establishing a read abundance value for the clinical sample read(s) in the biological sample by using the mode k-mer value(s) obtained greater than zero to calculate the proportion of reads shared between each clinical sample and the biological sample; and
(g2) repeating step (f2) for each additional clinical sample of step (e2).

10. The method of claim 9, wherein step (ii) comprises an all-verse-all comparison of the sequencing reads from the biological sample and the clinical sample or samples.

11. The method of claim 3 further comprising quality trimming, length filtering, sequencing adapter removal, binning of reads by molecular barcode, removal of human reads, or a combination thereof.

12. The method of claim 1, wherein counts for k-mers greater than two standard deviations from the mean of all k-mer counts from a sequencing read are removed prior to calculating the mode value.

13. The method of claim 12, wherein counts for k-mers that appear and disappear in technical replicates of the same sample are set to zero during creation of the read abundance values.

14. The method of claim 1, further comprising sequencing the DNA of the biological sample prior to deconstructing the sequencing reads.

15. The method of claim 14, further comprising isolating total DNA from the biological sample and removing human DNA from the isolated total DNA prior to sequencing, wherein the remaining DNA comprises microbial DNA.

16. The method of claim 15 further comprising fragmenting the microbial DNA, optionally ligating sequencing platform-specific adaptors to the microbial DNA prior to sequencing, and optionally indexing the sequenced microbial DNA.

17. The method of claim 1, wherein the treatment comprises administering the subject an antibiotic.

18. The method of claim 1, wherein steps (d1) and (e1) are performed.

19. A method comprising:
(i) obtaining a plurality of sequencing reads of DNA from a biological sample of a subject suspected of containing an infection;
(ii) computer-implemented steps of:
(a1) deconstructing all of the sequencing reads from the biological sample into unique k-mers;
(b1) counting the frequency of each unique k-mer from the biological sample and generating an index that maps the unique k-mers to the frequency count of that k-mer in the biological sample;
(c1) optionally excluding from the index,
k-mers with high counts having greater than two standard deviations from the mean of all k-mer counts from a sequencing read,
k-mers with low counts that appear and disappear in technical replicates of the same sample,
or a combination thereof;
(d1) optionally determining an overall frequency for each sequencing read in the biological sample, wherein the overall frequency is calculated by computing the mode frequency of all k-mers in the read using the index generated in (b1) and optionally as modified in (c1);
(e1) optionally removing reads based on frequency values computed in (d1), wherein analyses is optionally tuned to include reads from organisms present at specific frequencies;
(f1) computing shared k-mers between the biological sample, one or more clinical samples, and/or one or more additional biological samples (sample i vs. sample j) using a suffix array; wherein the resulting frequency data are normalized by averaging the shared sequence space and total sequence space between sample i and sample j; wherein the normalized frequency data are used to construct a matrix of normalized shared sequence space between the samples;
(g1) optionally repeating steps (a1)-(f1) with sequencing reads of DNA from one or more additional biological samples and/or clinical samples; wherein the clinical sample(s) are from patient(s) with known clinical outcomes, the biological sample(s) are from patient(s) with unknown clinical outcomes, and the clinical and biological samples are compared to determine the similarity of shared sequence space among samples;
(h1) constructing one or more matrix(s) of relational covariates derived from clinical parameters associated with the patient(s) that the sample(s) were derived from; optionally wherein comparisons between clinical covariates are Boolean and/or continuous values that are categorized and compared between samples based on high or low values that are clinically meaningful;
(i1) using a network modeling framework to compute the average amount of sequence space shared across the network for each sample i, and similarity of shared sequence amount among samples,
wherein the network modeling framework optionally includes, but is not limited to, a Bayesian inferential approach comprising measuring the distance and similarity between samples i and j;
(j1) estimating clinical parameters in the model using eigen value decomposition and regression; optionally wherein the relational covariates comprises a matrix comprising shared sequence space computed in steps (a1)-(f1); optionally wherein the joint posterior distribution of the parameters are examined via a Markov chain; optionally wherein clinical parameters included in the network are evaluated based on posterior confidence intervals of regression coefficients;

(k1) optionally visualizing each sample's position ($z_i$) in a k-dimensional latent space Z after a Procrustes' transformation to convert them into a similar grid to compare, where sample i and sample j are considered similar if they are close in that space;

(iii) prognosing the infection comprising using the network modeling as a representation of the similarity between the biological sample and associated clinical parameters and prior clinical samples and associated clinical parameters, the correlation of which is used to predict the outcome of the suspected infection in the biological sample from clinical samples;

and (iv) providing a treatment to the subject for the infection, wherein the treatment comprises administration of an antimicrobial agent, pressure bandage, negative pressure therapy, or a combination thereof, and is predicted to have a positive impact on the infection based upon the prognosis thereof.

20. The method of claim 19, wherein the network modeling framework (i1) comprises constructing an n×n symmetric matrix of shared sequence space between unknown biological sample(s) and known clinical sample(s), and an n×n×p array of clinical variables as regressors, to approximate the posterior distribution of parameters as an eigenmodel; wherein a Bayesian network analysis and Markov chain are used to represent the distance between samples using shared sequence data and clinical factors simultaneously.

* * * * *